US012806151B2

(12) United States Patent
Jermy et al.

(10) Patent No.: US 12,806,151 B2

(45) Date of Patent: *Nov. 24, 2026

(54) METHOD FOR TREATING BLASTOCYSTIS

(71) Applicant: Imam Abdulrahman Bin Faisal University, Dammam (SA)

(72) Inventors: B. Rabindran Jermy, Dammam (SA); Vijaya Ravinayagam, Dammam (SA); Ayman A. Elbadry, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 290 days.

This patent is subject to a terminal disclaimer.

(21) Appl. No.: 18/810,596

(22) Filed: Aug. 21, 2024

(65) Prior Publication Data

US 2024/0408030 A1 Dec. 12, 2024

Related U.S. Application Data

(62) Division of application No. 18/193,692, filed on Mar. 31, 2023, now Pat. No. 12,109,315, which is a division of application No. 17/842,876, filed on Jun. 17, 2022, now Pat. No. 11,826,477.

(51) Int. Cl.

| | |
|---|---|
| ***A61K 9/51*** | (2006.01) |
| ***A61K 31/05*** | (2006.01) |
| ***A61K 31/12*** | (2006.01) |
| ***A61P 33/00*** | (2006.01) |

(52) U.S. Cl.

CPC ............ *A61K 9/5115* (2013.01); *A61K 31/05* (2013.01); *A61K 31/12* (2013.01); *A61P 33/00* (2018.01)

(58) Field of Classification Search

None

See application file for complete search history.

(56) References Cited

U.S. PATENT DOCUMENTS

| | | | | |
|---|---|---|---|---|
| 6,103,262 | A * | 8/2000 | Desai | A61K 31/415 424/501 |
| 11,065,344 | B2 | 7/2021 | Alsaiari et al. | |
| 11,090,617 | B2 | 8/2021 | Yamada et al. | |
| 11,096,911 | B2 | 8/2021 | Jermy et al. | |
| 11,826,477 | B1 * | 11/2023 | Jermy | A61K 31/05 |

(Continued)

FOREIGN PATENT DOCUMENTS

| | | | | |
|---|---|---|---|---|
| CN | 107383386 B | 7/2020 | | |
| WO | WO-2020210367 A1 * | 10/2020 | | A61K 31/704 |

OTHER PUBLICATIONS

Davood. Dorostkar Moghaddam et al. "Blastocystis hominis and the evaluation of efficacy of metronidazole and trimethoprim/sulfamethoxazole." Parasitology Research, vol. 96, 2005, pp. 273-275. (Year: 2005).*

(Continued)

*Primary Examiner* — Isaac Shomer

(74) *Attorney, Agent, or Firm* — Oblon, McClelland, Maier & Neustadt, L.L.P.

(57) ABSTRACT

A nanomedicinal composition comprising a nanocarrier and an antioxidant. The nanocarrier contains a metal organic framework and a porous silicate and/or aluminosilicate matrix. The antioxidant is disposed in the pores and/or on the surface of the nanocarrier by a solution phase impregnation process. The nanomedicinal composition is used in a method of treating *Blastocystis* infection.

13 Claims, 8 Drawing Sheets

Novel nanocomposites

(56) References Cited

U.S. PATENT DOCUMENTS

| | | | | |
|---|---|---|---|---|
| 12,109,315 | B2 * | 10/2024 | Jermy | A61K 31/05 |
| 12,280,158 | B2 * | 4/2025 | Jermy | A61K 9/5115 |
| 2006/0034763 | A1 | 2/2006 | Chen | |
| 2011/0033525 | A1 * | 2/2011 | Liu | A61K 47/26 977/773 |
| 2018/0280303 | A1 * | 10/2018 | Jermy | A61K 31/192 |
| 2020/0179243 | A1 | 6/2020 | Dutta et al. | |

OTHER PUBLICATIONS

CAS Registry Record for Curcumin (CAS # 458-37-7). Obtained by examiner on Aug. 7, 2024, entered STN Nov. 16, 1984, 6 printed pages. (Year: 2024).*

CAS Registry Record for Resveratrol (CAS # 501-36-0). Obtained by examiner on Aug. 7, 2024, entered STN Nov. 16, 1984, 6 printed pages. (Year: 2024).*

Aziza A. M. El-Shafey, et al., "Curcumin@metal organic frameworks nano-composite for treatment of chronic toxoplasmosis", Journal of Materials Science: Materials in Medicine, vol. 31, Article No. 90, Oct. 21, 2020, pp. 1-13.

Yumei Xiao, et al., "a-lipoic acid (α-lip) modification on surface of nano-scaled zeolitic imidazole Framework-8 for enhanced drug delivery", Journal of Solid State Chemistry, vol. 292, Aug. 22, 2020, 3 pages (Abstract only).

Rajesh Kotcherlakota et al. "Curcumin loaded mesoporous silica: an effective drug delivery system for cancer treatment." Biomaterials Science, vol. 4, 2016, pp. 448-459. (Year: 2016).

Zhiping Lai. "Development of ZIF-8 membranes: opportunities and challenges for commercial applications." Current Opinion in Chemical Engineering, vol. 20, 2018, pp. 78-85. (Year: 2018).

Mona Abdel-Fattah Ahmed et al. "In Vitro Activity of Curcumin and Silver Nanoparticles Against Blastocystis hominis." Infectious Diseases in Clinical Practice, vol. 23, No. 3, May 2015, pp. 135-140. (Year: 2015).

Murtala Bindawa Isah & Mohammed Auwal Ibrahim. "The role of antioxidants treatment on the pathogenesis of malarial infections: a review." Parasitology Research, vol. 113, 2014, pp. 801-809. (Year: 2014).

* cited by examiner

METHOD FOR TREATING BLASTOCYSTIS

CROSS-REFERENCE TO RELATED APPLICATIONS

The present application is a Continuation of U.S. application Ser. No. 18/193,692, now U.S. Pat. No. 12,109,315, having a filing date of Mar. 31, 2023 which is a Division of U.S. application Ser. No. 17/842,876, now U.S. Pat. No. 11,826,477, having a filing date of Jun. 17, 2022.

BACKGROUND OF THE INVENTION

Field of the Invention

The present disclosure relates to a nanomedicinal composition comprising a nanocarrier and an antioxidant, a method of its preparation, and a method of treating an infection by parasite in the genus *Blastocystis.*

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Parasitic diseases are a major public health threat in Saudi Arabia and worldwide. These diseases are responsible for considerable morbidity and mortality. *Blastocystis* is a unicellular parasitic protozoon. It inhabits the large intestine of humans and animals, and is detected globally, with up to 100% prevalence [El Safadi, D., et. al., BMC Infect Dis., 2016, 26, 451]. Blastocystosis, human infection by *Blastocystis*, has various outcomes: it can be asymptomatic in infected patients, can produce diarrhea and other gastrointestinal symptoms, or have an opportunistic character and cause infection in immunocompromised patients. *Blastocystis* has been linked to symptoms of inflammatory bowel diseases, irritable bowel syndrome and acute urticaria [Katsarou-Katsari, A., et. al., Acta Derm Venereo. 2008, 88, 80-81; & Roberts, T., et. al., Gut Pathogens, 2014, 6, 1, 17]. Recently, *Blastocystis* was linked to gut dysbiosis and associated gut disorders as well as the induction of growth of colon and rectum cancer by apoptosis of cancer colon cells [Tan, T. C., et. al., Parasitol Res., 2009, 105, 1283-1286; Chandramathi, S., et. al., Parasitol Res., 2020, 106, 4, 941-945; & Stensvold, C. R., et. al., Trends Parasitol., 2020, 3, 315-316].

Drugs currently used to treat *Blastocystis* are not fully effective. Among the many drugs used to treat *Blastocystis* infection, metronidazole is the most effective therapy, however, there remains controversy about responses of different categories of diarrheic patients in addition to side effects and drug resistance [Rajamanikam, A., et. al., PLoS One, 2019, 14, 2, e0212542]. Some antioxidant compounds have exhibited activity against *Blastocystis*, but the bioavailability of most effective antioxidant compounds is too low to be clinically useful. Consequently, there is a vital need to develop effective alternative therapies to treat and control this disease.

Accordingly, it is an objective of the present disclosure to provide a nanocarrier for certain antioxidant compounds with the aim of providing a method of treating *Blastocystis* infection.

SUMMARY OF THE INVENTION

The present disclosure relates to a nanomedicinal composition, comprising a nanocarrier comprising a metal organic framework which is a zeolitic imidazolate framework, and a porous silicate and/or aluminosilicate matrix, and an antioxidant disposed in the pores and/or on a surface of the nanocarrier.

In some embodiments, the porous silicate and/or aluminosilicate matrix is at least one selected from the group consisting of MCM-41 and KIT-6.

In some embodiments, the nanocarrier has a surface area of 225 to 750 $m^2/g$, a pore volume of 0.25 to 0.85 $cm^3/g$, and a mean pore size of 2 to 10 nm.

In some embodiments, the porous silicate and/or aluminosilicate matrix is MCM-41 and the nanocarrier has a surface area of 450 to 750 $m^2/g$, a pore volume of 0.25 to 0.65 $cm^3/g$, and a mean pore size of 2 to 4 nm.

In some embodiments, the porous silicate and/or aluminosilicate matrix is KIT-6 and the nanocarrier has a surface area of 225 to 450 $m^2/g$, a pore volume of 0.45 to 0.85 $cm^3/g$, and a mean pore size of 5 to 10 nm.

In some embodiments, the porous silicate and/or aluminosilicate matrix is present in an amount of 1 to 20 wt % based on a total weight of the nanocarrier.

In some embodiments, the metal organic framework comprises an imidazole of formula I:

(I)

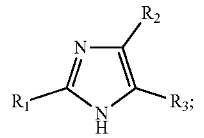

and is substantially free of a benzimidazole of formula II:

(II)

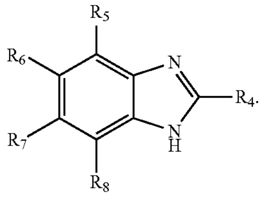

In some embodiments, the zeolitic imidazolate framework is ZIF-8.

In some embodiments, the antioxidant is at least one selected from the group consisting of quercetin, rutin, coenzyme Q10, gallic acid, resveratrol, and curcumin.

In some embodiments, the antioxidant is curcumin.

In some embodiments, the antioxidant is resveratrol.

In some embodiments, the antioxidant is present in the nanomedicinal composition in an amount of 5 to 50 wt %, based on a total weight of nanomedicinal composition.

In some embodiments, the nanomedicinal composition releases greater than 20% of a total weight of curcumin within 24 to 72 hours of contact with a suitable biological medium.

In some embodiments, the nanomedicinal composition releases greater than 7.5% of a total weight of resveratrol within 24 to 72 hours of contact with a suitable biological medium.

In some embodiments, the nanomedicinal composition reduces the viability of *Blastocystis* organisms by at least 75% when the nanomedicinal composition is present for 24 hours in an amount of 0 to 1000 μg/mL.

The present disclosure also relates to a method of forming the nanomedicinal composition comprising mixing the metal organic framework and the porous silicate and/or aluminosilicate matrix to form the nanocarrier, combining the nanocarrier and the antioxidant in an impregnation solution thereby forming the nanomedicinal composition, and isolating the nanomedicinal composition.

In some embodiments, the mixing comprises ultrasonication.

In some embodiments, the impregnation solution comprises an alcohol having 1 to 5 carbon atoms and the antioxidant is present in an amount of 0.5 to 3 mg/mL of impregnation solution.

The present disclosure also relates to a method for treating an infection by a parasite in the genus *Blastocystis* in a subject, comprising administering to a subject in need of therapy a pharmaceutical composition comprising the nanomedicinal composition.

The present disclosure also relates to a pharmaceutical composition, comprising the nanomedicinal composition of claim 1 and a pharmaceutically acceptable excipient.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
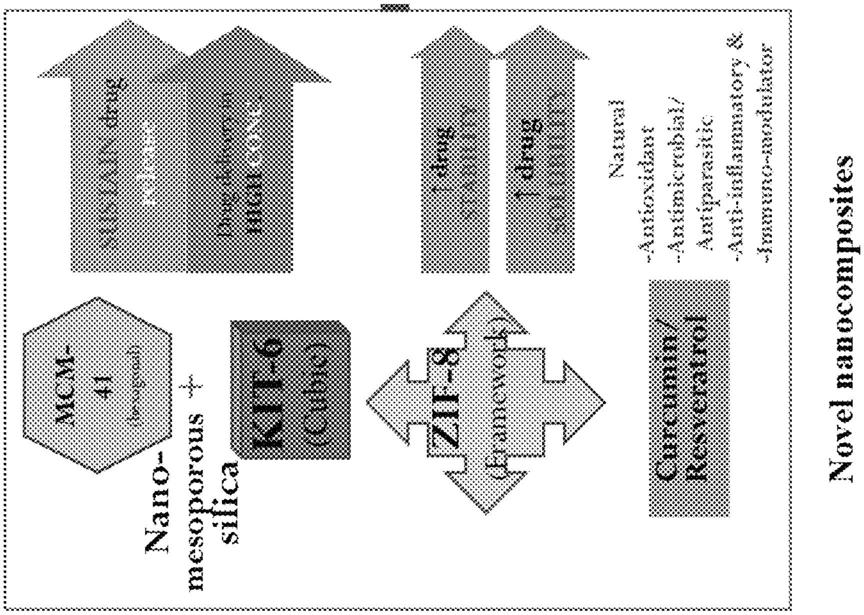
FIG. 1 shows a schematic overview of the present invention.

In the following description, it is understood that other embodiments may be utilized and structural and operational changes may be made without departure from the scope of the present embodiments disclosed herein.

DEFINITIONS

Embodiments of the present disclosure will now be described more fully hereinafter with reference to the accompanying drawings, in which some, but not all embodiments of the disclosure are shown.

As used herein, the words "a" and "an" and the like carry the meaning of"one or more". Within the description of this disclosure, where a numerical limit or range is stated, the endpoints are included unless stated otherwise. Also, all values and subranges within a numerical limit or range are specifically included as if explicitly written out.

As used herein, the terms "optional" or "optionally" means that the subsequently described event(s) can or cannot occur or the subsequently described component(s) may or may not be present (e.g., 0 wt. %).

The phrase "substantially free", unless otherwise specified, describes an amount of a particular component (e.g., a benzimidazole of Formula (II)), that when present, is present in an amount of less than about 1 wt. %, preferably less than about 0.5 wt. %, more preferably less than about 0.1 wt. %, even more preferably less than about 0.05 wt. %, relative to a total weight of the composition being discussed, and also includes situations where the composition is completely free of the particular component (i.e., 0/o wt.).

As used herein, the term "alkyl" unless otherwise specified refers to both branched and straight chain saturated aliphatic primary, secondary, and/or tertiary hydrocarbon fragments of typically $C_1$ to $C_{20}$. Non-limiting examples of such hydrocarbon fragments include methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "alkoxy" refers to a straight or branched chain alkoxy including, but not limited to, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy.

The term "halogen", as used herein, means fluoro, chloro, bromo and iodo.

As used herein, the term "substituted" refers to at least one hydrogen atom is replaced with a non-hydrogen group, provided that normal valencies are maintained and that the substitution results in a stable compound. When a R group (denoted as $R_1$, $R_2$, and so forth) is noted as "optionally substituted", the substituents are selected from the exemplary group including, but not limited to, halogen (e.g., chlorine, bromine, fluorine or iodine), alkoxy (i.e., straight chain alkoxy having 1 to 3 carbon atoms, and includes, for example, methoxy, ethoxy, and propoxy), hydroxy, amino, alkylamino, thiol, alkylthio, sulfonamido (e.g., $—SO_2NH_2$), substituted sulfonamide (e.g., $—SO_2NHalkyl$ or cases where there are two alkyl substituents on one nitrogen), nitro, cyano, carboxy, carbamyl (e.g., $—CONH_2$), substituted carbamyl (e.g., —CONHalkyl or cases where there are two alkyl substituents on one nitrogen), and mixtures thereof. The substituents may be either unprotected, or protected as necessary, as known to those skilled in the art, for example, as taught in Greene et al., "Protective Groups in Organic Synthesis". John Wiley and Sons, Second Edition, 1991, hereby incorporated by reference in its entirety).

According to a first aspect, the present disclosure relates to a nanomedicinal composition, comprising a nanocarrier comprising a metal organic framework, and a porous silicate and/or aluminosilicate matrix, and an antioxidant disposed in the pores and/or on a surface of the nanocarrier.

The International Union of Pure and Applied Chemistry (IUPAC) states that a metal organic framework (MOF) is a coordination network with organic ligands containing potential voids. A coordination network is a coordination compound extending, through repeating coordination entities, in one dimension, but with cross-links between two or more individual chains, loops, or spiro-links, or a coordination compound extending through repeating coordination entities in two or three dimensions; and finally a coordination polymer is a coordination compound with repeating coordination entities extending in one, two, or three dimensions. A coordination entity is an ion or neutral molecule that is composed of a central atom, usually that of a metal, to which is attached a surrounding array of atoms or groups of atoms, each of which is called ligands. More succinctly, a metal organic framework is characterized by metal ions or clusters coordinated to organic ligands to form one-, two-, or three-dimensional structures. Typically, a MOF exhibits a regular void or pore structure. The nature of the void or pore structure, including properties or structural factors such as the geometry about the metal ions or clusters, the arrangement of the linkages between metal ions or clusters, and the number, identity, and spatial arrangement of voids or pores. These properties may be described as the structure of the repeat units and the nature of the arrangement of the repeat units. The specific structure of the MOF, which may include the void or pore structure is typically referred to as the MOF topology.

The metal-organic framework comprises a metal ion which is an ion of at least one metal selected from the group consisting of a transition metal (e.g. Sc, Ti, V, Cr, Mn, Fe, Co, Ni, Cu, Y, Zr, Nb, Mo, Tc, Ru, Rh, Pd, Ag, Hf, Ta. W, Re, Os, Ir, Pt, Au, Rf, Db, Sg, Bh, Hs, Mt, Ds, Rg, and Cn), a post-transition metal (e.g. Al, In, Ga, Sn, Bi, Pb, Tl, Zn, Cd, and Hg), and an alkaline earth metal (e.g. Be, Mg, Ca, Sr. Ba, and Ra). Further, these metal ions may be of any oxidation state $M^{+1}$, $M^{+2}$, $M^{+3}$, etc. In one or more embodiments, the metal ion is an ion of at least one metal selected from the group consisting of Zn, Cu, Fe, Ni, Co, Mn, Cr, Cd, Mg, Ca, and Zr. In a preferred embodiment, the at least one metal is Zn.

In the formation of a metal organic framework, the organic ligands must meet certain requirements to form coordination bonds, primarily being multi-dentate, having at least two donor atoms (i.e. N-, and/or O-) and being neutral or anionic. The structure of the metal organic framework is also affected by the shape, length, and functional groups present in the organic linker. In certain embodiments, the metal organic framework of the present disclosure comprises anionic ligands as organic ligands. In one or more embodiments, the organic ligands may have at least two nitrogen donor atoms. For example, the organic ligands may be imidazolate-based, imidazole-derived or ligands similar to an imidazole including, but not limited to, optionally substituted imidazoles, optionally substituted benzimidazoles, optionally substituted imidazolines, optionally substituted pyrazoles, optionally substituted thiazoles, and optionally substituted triazoles. In a preferred embodiment, the metal organic framework of the present disclosure in any of its embodiments comprises 2-methylimidazole and 5-methylbenzimidazole as the organic ligands. 2-Methylimidazole and 5-methylbenzimidazole organic ligands have free nitrogen atoms that may each form a coordinative bond to the metal ions (e.g. Zn(II)) to produce a coordination network.

In one or more embodiments, the ligand comprises an imidazole of formula (I) and/or a benzimidazole of formula (II):

(I)

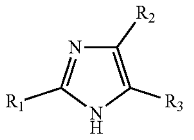

(II)

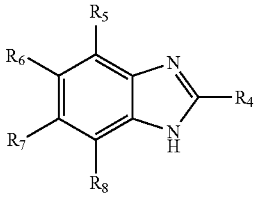

wherein $R_1$, $R_2$, $R_3$, $R_4$, $R_5$, $R_6$, $R_7$, and $R_8$ are each independently selected from the group consisting of a hydrogen, an optionally substituted alkyl, an optionally substituted cycloalkyl, an optionally substituted alkoxy, a hydroxyl, a halogen, a nitro, and a cyano. Preferably, $R_1$, $R_2$, $R_3$, $R_4$, $R_5$, $R_6$, $R_7$, and $R_8$ are each independently a hydrogen, an optionally substituted $C_1$-$C_3$ alkyl group, or an optionally substituted $C_3$-$C_6$ cycloalkyl group. More preferably, $R_1$, $R_2$, $R_3$, $R_4$, $R_5$, $R_6$, $R_7$, and $R_8$ are each independently a hydrogen or a methyl.

Exemplary imidazole-based ligands that may be applicable to the current disclosure include, but are not limited to, imidazole, 2-methylimidazole, 4-methylimidazole, 2-ethylimidazole, 2-isopropylimidazole, 4-tert-butyl-1H-imidazole, 2-ethyl-4-methylimidazole, 2-bromo-1H-imidazole, 4-bromo-1H-imidazole, 2-chloro-1H-imidazole, 2-iodoimidazole, 2-nitroimidazole, 4-nitroimidazole, (1H-imidazol-2-yl)methanol, 4-(hydroxymethyl)imidazole, 2-aminoimidazole, 4-(trifluoromethyl)-1H-imidazole, 4-cyanoimidazole, 3H-imidazole-4-carboxylic acid, 4-imidazolecarboxylic acid, imidazole-2-carboxylic acid, 2-hydroxy-1H-imidazole-4-carboxylic acid, 4,5-imidazoledicarboxylic acid, 5-iodo-2-methyl-1H-imidazole, 2-methyl-4-nitroimidazole, 2-(aminomethyl)imidazole, 4,5-dicyanoimidazole, 4-imidazoleacetic acid, 4-methyl-5-imidazolemethanol, 1-(4-methyl-H-imidazol-5-yl)methanamine, 4-imidazoleacrylic acid, 5-bromo-2-propyl-1H-imidazole, ethyl-(1H-imidazol- 2-ylmethyl)-amine, and 2-butyl-5-hydroxymethylimidazole. In preferred embodiments, the imidazole of formula (I) is 2-methylimidazole.

Exemplary benzimidazole-based ligands that may be applicable to the current disclosure include, but are not limited to, benzimidazole, 5-methylbenzimidazole, 2-methylbenzimidazole, 5-chlorobenzimidazole, 5-bromobenzimidazole, 5,6-dimethylbenzimidazole, 5-methoxybenzimidazole, 2-chlorobenzimidazole, 2-bromo-1H-benzimidazole, 6-bromo-1H-benzimidazole, 5-fluoro-1H-benzimidazole, 5-chloro-2-methylbenzimidazole, methyl benzimidazole-2-acetate, 1H-benzoimidazol-4-ol, 1H-benzimidazol-5-yl-methanol, 2-benzimidazolemethanol, 4-chloro-6-(trifluoromethyl)benzimidazole, 5-chloro-2-(trichloromethyl) benzimidazole, 5-cyanobenzimidazole, (2-benzimidazolyl) acetonitrile, (5-chloro-1H-benzimidazol-2-yl)methanol, 2-(chloromethyl)benzimidazole, 5-iodo-2-methylbenzimidazole, (5-chloro-1H-benzimidazol-2-yl)methylamine, 2-(aminomethyl)benzimidazole, 2-(6-chloro-1H-benzimidazol-2-yl)ethanol, 2-(1H-benzoimidazol-2-yl)-acetamide, (6-methoxy-1H-benzimidazol-2-yl)methanol, 5,6-dimethoxybenzimidazole, 2-(1H-benzoimidazol-2-yl)-ethylamine, 1-(5-methyl-1H-benzimidazol-2-yl)methanamine, 1-(5-methyl-1H-benzimidazol-2-yl)ethanamine, 2-benzimidazolepropionic acid, 2-(5-methyl-1H-benzimidazol-2-yl)ethanamine, 2-(3-hydroxy-N-propyl)-5-(trifluoromethyl)-benzimidazole, and N-methyl-1-(5-methyl-1H-benzimidazol-2-yl)methanamine. In some embodiments, the benzimidazole of formula (II) is 5-methylbenzimidazole.

In one or more embodiments, the metal organic framework comprises a imidazole of formula (I). In one or more embodiments, the metal organic framework is substantially free of a benzimidaxole of formula (II).

Metal organic frameworks comprising such imidazole or benzimidazole ligands are typically referred to as zeolitic imidazolate frameworks. In some embodiments, the metal organic framework is a zeolitic imidazolate framework. In one or more embodiments, the metal-organic framework comprises ZIF-8. In preferred embodiments, the metal-organic framework is ZIF-8. Other metal-organic frameworks that may be used in the currently disclosed membrane include, but are not limited to, isoreticular metal organic framework-3 (IRMOF-3), MOF-69A, MOF-69B, MOF-69C, MOF-70, MOF-71, MOF-73, MOF-74, MOF-75, MOF-76, MOF-77, MOF-78, MOF-79, MOF-80, DMOF-1-NH2, UMCM-1-NH2, MOF-69-80, ZIF-1, ZIF-2. ZIF-3, ZIF-4, ZIF-5, ZIF-6, ZIF-7, ZIF-9, ZIF-10. ZIF-11, ZIF-12, ZIF-14, ZIF-20, ZIF-21, ZIF-22, ZIF-23, ZIF-25, ZIF-60, ZIF-61, ZIF-62, ZIF-63, ZIF-64, ZIF-65, ZIF-66, ZIF-67, ZIF-68. ZIF-69, ZIF-70, ZIF-71, ZIF-72, ZIF-73, ZIF-74, ZIF-75, ZIF-76, ZIF-77, ZIF-78, ZIF-79, ZIF-80, ZIF-81, ZIF-82, ZIF-90, ZIF-91. ZIF-92, ZIF-93, ZIF-94, ZIF-96, ZIF-97, ZIF-100, ZIF-108, ZIF-303, ZIF-360, ZIF-365, ZIF-376, ZIF-386, ZIF-408, ZIF-410, ZIF-412, ZIF-413, ZIF-414, ZIF-486, ZIF-516, ZIF-586, ZIF-615, and ZIF-725.

In some embodiments, the metal organic framework is present in the form of particles. In general, the metal organic framework particles can be any shape known to one of ordinary skill in the art. Examples of suitable shapes the metal organic framework particles may take include spheres, spheroids, lentoids, ovoids, solid polyhedra such as tetrahedra, cubes, octahedra, icosahedra, dodecahedra, rectangular prisms, triangular prisms (also known as nanotriangles), nanoplatelets, nanodisks, blocks, flakes, discs, granules, angular chunks, and mixtures thereof. Nanorods or nanowires are not a shape that the metal organic framework particles are envisioned as having in any embodiments.

In some embodiments, the metal organic framework particles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of metal organic framework particles having a different shape. As used herein, the term "non-uniform shape" refers to an average consistent shape that differs by more than 10% of the distribution of metal organic framework particles having a different shape. In one embodiment, the shape is uniform and at least 90% of the metal organic framework particles are spherical or substantially circular, and less than 10% are polygonal. In another embodiment, the shape is non-uniform and less than 90% of the metal organic framework particles are spherical or substantially circular, and greater than 10% are polygonal.

In some embodiment, the metal organic framework is in the form of particles having a mean particle size of 50 to 10,000 nm, preferably 75 to 9,000 nm, preferably 100 to 8,000 nm, preferably 125 to 7,500 nm preferably 150 to 7,000 nm. In embodiments where the metal organic framework particles are spherical, the particle size may refer to a particle diameter. In embodiments where the metal organic framework particles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass. In some embodiments where the metal organic framework particles have an anisotropic shape such as nanorods or nanotubes, the particle size may refer to a length of the nanorod or nanotube, a width of the nanorod or nanotube, or an average of the length and width of the nanorod or nanotube. In some embodiments, the particle size refers to the diameter of a sphere having an equivalent volume as the particle.

In general, any suitable silicate and/or aluminosilicate matrix known to one of ordinary skill in the art may be used in the nanomedicinal composition. Examples of such suitable porous silica, silicate, or aluminosilicate materials include, but are not limited to, MCM-41, MCM-48, Q-10 silica, hydrophobic silica, mesobeta, mesoZSM-5, SBA-15, KIT-5, KIT-6, mesosilicalite, hierarchical porous silicalite, SBA-16, mesoporous silica spheres, and halloysite. The term "silicate matrix" should be understood to include silica itself. Methods of obtaining the various types porous silica, silicate, or aluminosilicate material are well-known in the art [see for example Gobin, Oliver Christian "SBA-16 Materials: Synthesis, Diffusion, and Sorption Properties" Dissertation, Laval University, Ste-Foy, Quebec, Canada, January 2006, in particular section 2.2; and U.S. patent application Ser. No. 15/478,794—both incorporated herein by reference in their entireties]. Aluminosilicate materials may be characterized by a ratio of Si to Al present in the material. In general, the aluminosilicate material may have any suitable Si:Al molar ratio. Examples of such suitable Si:Al molar ratios are 1000:1 to 1:250, preferably 500:1 to 1:200, preferably 250:1 to 1:100, preferably 150:1 to 1:75, preferably 100:1 to 1:50, preferably 50:1 to 1:25, preferably 25:1 to 1:10, preferably 10:1 to 1:5, preferably 5:1 to 1:2.5, preferably 2.5:1 to 1:1.5, preferably 1.5:1 to 1:1. In general, the elemental composition of the silicate and/or aluminosilicate material, including the Si:Al molar ratio, may be determined by any suitable technique known to one of ordinary skill in the art. Examples of suitable such techniques include mass spectrometry techniques such as inductively-coupled plasma mass spectrometry (ICP-MS), atomic emission spectroscopy techniques such as inductively-coupled plasma atomic emission spectroscopy (ICP-AES) (also referred to as ICP optical emission spectroscopy, ICP-OES), atomic absorption spectroscopy techniques such as inductively-coupled plasma atomic absorption spectroscopy (ICP-AAS), and X-ray spectroscopy techniques such as X-ray photoelectron spectroscopy.

Silicates and aluminosilicates are materials which comprise $SiO_4$ tetrahedra (and $AlO_4^-$ tetrahedra, $AlO_6$ octahedra, and/or $Al(OH)_6$ octahedra in the case of aluminosilicates) joined together in a wide variety of structural motifs. The tetrahedra (and if applicable octahedra) in the silicate and/or aluminosilicate material of the present invention may in general adopt any structural motif present in other silicate materials, such as isolated tetrahedra as in neosilicates (single tetrahedra, also called orthosilicates) and sorosilicates (double tetrahedra), chains of tetrahedra such as inosilicates (both single chain as in pyroxene group silicates and double chain as in amphibole group silicates), rings of tetrahedra as in cyclosilicates, sheets of tetrahedra as in phyllosilicates, and three-dimensional frameworks as in tectosilicates. In some aluminosilicates, the material comprises a substructure comprising silicon-containing and/or aluminum-containing tetrahedral and a substructure comprising aluminum-containing octahedral. An example of such an arrangement is the mineral kaolin, which comprises sheets of alternating tetrahedra-containing layers and octahedra-containing layers. The arrangement of isolated tetrahedra, chains of tetrahedra, sheets of tetrahedra, or three-dimensional frameworks may give rise to channels, pores, cages, or other spaces within the silicate and/or aluminosilicate which is capable of hosting material which is not the silicate and/or aluminosilicate itself. Examples of materials, particularly those relevant to the current disclosure, include water, organic molecules, and inorganic nanoparticles. While the larger structures formed of tetrahedra (i.e. chains, rings, sheets, and three-dimensional frameworks) may themselves be ordered, the arrangement of these larger structures may be disordered. Such disorder may give rise to a material which is amorphous by techniques for determining crystallinity or crystal structure such as powder X-ray diffraction (PXRD). Alternatively, the larger structures may be ordered, giving rise to a crystalline material.

MCM-41 (Mobil Composition of Matter No. 41) is a mesoporous silica material with a hierarchical structure from a family of silicate and aluminosilicate solids that were developed by researchers at Mobil Oil Corporation and that can be used as catalysts or catalyst supports. MCM-41 and MCM-48 both comprise an amorphous silica wall and possess long range ordered framework with uniform mesopores. These materials also possess large surface area, which can be up to more than 1,000 $m^2g^{-1}$. The pore diameter of these materials can be controlled to fall within a mesoporous range between 1.5 and 20 nm by adjusting the synthesis conditions and/or by employing surfactants with different chain lengths in their preparation. In embodiments where the porous silicate matrix is MCM-41, the nanocarrier may be referred to as a "MCM-41 nanocarrier".

KIT-6 is a mesoporous silica material. KIT-6 has a bicontinuous cubic mesostructure with Ia3d symmetry. KIT-6 is characterized by an interpenetrating cylindrical pore system. Such pores typically have a pore size from about 3.5 to about 18.5 nm and can be controlled by various parameters during the synthesis such as synthesis temperature.

In some embodiments, the porous silicate and/or aluminosilicate matrix is surface modified prior to use in the nanocarrier. Such surface modifications may change the surface properties of the porous silicate and/or aluminosilicate matrix, for example by increasing or decreasing the number or concentration of functional groups found on an unmodified porous silicate and/or aluminosilicate matrix or by introducing new functional groups to the porous silicate and/or aluminosilicate matrix. Examples of such new functional groups include, but are not limited to carboxylic acid or carboxylate groups, amine or ammonium groups, sulfo groups, and phosphate groups. Such functional groups may be charged or uncharged. In some embodiments, the surface modification changes the surface charge of the interior surface, the exterior surface, the pore surface, or any combination thereof of the modified porous silicate and/or aluminosilicate matrix compared to unmodified porous silicate and/or aluminosilicate matrix. Preferably, the surface modification does not change the surface charge of the interior surface, exterior surface, pore surface, or any combination thereof of the modified porous silicate and/or aluminosilicate matrix compared to unmodified porous silicate and/or aluminosilicate matrix. Such surface modification may be performed using any suitable method or with any suitable surface modifying agent or agents known to one of ordinary skill in the art. One example of such a method is the use of silanes or organosilicates bearing one or more functional groups to be added by the surface modification. Such surface modification may result in said functional groups being attached to the porous silicate and/or aluminosilicate matrix by covalent bonds. Alternatively, said functional groups may be attached to the porous silicate and/or aluminosilicate matrix by a non-covalent interaction, for example electrostatic interaction, physisorption, or hydrogen bonding. In some embodiments, the surface modifying agent(s) are substantially free of silanes. In some embodiments, the surface modifying agent(s) are substantially free of organosilicates. In some embodiments, the surface modifying agent(s) are substantially free of amino acids. In some embodiments, the surface modifying agent(s) are substantially free of short peptides (i.e. 2-20 residues). In some embodiments, the surface modifying agent(s) are substantially free of chromium salts (chrome alum, chromium acetate, etc.); calcium salts (calcium chloride, calcium hydroxide, etc.); aluminum salts (aluminum chloride, aluminumhydroxide, etc.); dialdehydes (glutaraldehyde, etc.); carbodiimides (EDC, WSC, N-hydroxy-5-norbornene-2,3-di-carboxylmide (HONB), N-hydroxysuccinic acid imide (HOSu), dicyclohexylcarbodiimide (DCC), etc.); N-hydroxysuccinimide; and/or phosphorus oxychloride. In some embodiments, the surface modifying agent(s) are substantially free of proteins. Examples of such proteins include, but are not limited to collagen, gelatin, albumin, ovalbumin, casein, transferrin, fibrin, and fibrinogen.

In some embodiments, the porous silicate and/or aluminosilicate matrix is present in the form of particles. In general, the porous silicate and/or aluminosilicate matrix particles can be any shape known to one of ordinary skill in the art. Examples of suitable shapes the porous silicate and/or aluminosilicate matrix particles may take include spheres, spheroids, lentoids, ovoids, solid polyhedra such as tetrahedra, cubes, octahedra, icosahedra, dodecahedra, rectangular prisms, triangular prisms (also known as nanotriangles), nanoplatelets, nanodisks, blocks, flakes, discs, granules, angular chunks, and mixtures thereof. Nanorods or nanowires are not a shape that the porous silicate and/or aluninosilicate matrix particles are envisioned as having in any embodiments.

In some embodiments, the porous silicate and/or aluminosilicate matrix particles have uniform shape. Alternatively, the shape may be non-uniform. As used herein, the term “uniform shape” refers to an average consistent shape that differs by no more than 10%, by no more than 5%, by no more than 4%, by no more than 3%, by no more than 2%, by no more than 1% of the distribution of porous silicate and/or aluminosilicate matrix particles having a different shape. As used herein, the term “non-uniform shape” refers to an average consistent shape that differs by more than 10% of the distribution of porous silicate and/or aluminosilicate matrix particles having a different shape. In one embodiment, the shape is uniform and at least 90% of the porous silicate and/or aluminosilicate matrix particles are spherical or substantially circular, and less than 10% are polygonal. In another embodiment, the shape is non-uniform and less than 90% of the porous silicate and/or aluminosilicate matrix particles are spherical or substantially circular, and greater than 10% are polygonal.

In some embodiment, the porous silicate and/or aluminosilicate matrix is in the form of particles having a mean particle size of 50 to 10,000 nm, preferably 75 to 9,000 nm, preferably 100 to 8,000 nm, preferably 125 to 7,500 nm preferably 150 to 7,000 nm. In embodiments where the porous silicate and/or aluminosilicate matrix particles are spherical, the particle size may refer to a particle diameter. In embodiments where the porous silicate and/or aluminosilicate matrix particles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass, in some embodiments where the porous silicate and/or aluminosilicate matrix particles have an anisotropic shape such as nanorods or nanotubes, the particle size may refer to a length of the nanorod or nanotube, a width of the nanorod or nanotube, or an average of the length and width of the nanorod or nanotube. In some embodiments, the particle size refers to the diameter of a sphere having an equivalent volume as the particle.

In some embodiments, the porous silicate and/or aluminosilicate matrix is present in an amount of 1 to 20 wt %, preferably 2 to 18 wt %, preferably 3 to 17 wt %, preferably 4 to 16 wt %, preferably 5 to 15 wt %, preferably 6 to 14 wt %, preferably 7 to 13 wt %, preferably 8 to 12,wt %, preferably 9 to 11 wt %, preferably 10 wt %, based on a total weight of the nanocarrier.

In some embodiments, the nanocarrier has a surface area of 225 $m^2/g$ to 750 m/g, preferably 250 $m^2/g$ to 725 $m^2/g$, preferably 275 $m^2/g$ to 700 $m^2/g$, preferably 300 $m^2/g$ to 675 $m^2/g$. In some embodiments, the porous silicate and/or aluminosilicate matrix is particles of MCM-41 and the nanocarrier has a surface area of 450 to 750 $m^2/g$, preferably 460 to 740 $m^2/g$, preferably 470 to 730 $m^2/g$, preferably 480 to 720 $m^2/g$, preferably 490 to 710 $m^2/g$, preferably 500 to 700 $m^2/g$, preferably 510 to 690 $m^2/g$, preferably 520 to 680 $m^2/g$, preferably 530 to 670 $m^2/g$, preferably 540 to 660 $m^2/g$, preferably 550 to 650 $m^2/g$, preferably 560 to 640 $m^2/g$, preferably 570 to 630 $m^2/g$, preferably 580 to 620 $m^2/g$, preferably 590 to 610 $m^2/g$. In some embodiments, the porous silicate and/or aluminosilicate matrix is particles of KIT-6 and the nanocarrier has a surface area of 225 to 450 $m^2/g$, preferably 235 to 440 $m^2/g$, preferably 245 to 430

$m^2/g$, preferably 255 to 420 $m^2/g$, preferably 265 to 410 $m^2/g$, preferably 275 to 400 $m^2/g$, preferably 285 to 390 $m^2/g$, preferably 295 to 380 $m^2/g$, preferably 305 to 370 $m^2/g$, preferably 315 to 360 $m^2/g$, preferably 325 to 350 $m^2/g$, preferably 335 to 340 $m^2/g$.

In some embodiments, the nanocarrier has a mean pore size of 1 nm to 60 nm, preferably 1.25 to 50 nm, preferably 1.5 nm to 40 nm, preferably 1.75 nm to 30 nm, preferably 2 nm to 20 nm, preferably 2.25 to 10 nm, preferably 2.5 to 9 am, preferably 2.75 to 8 nm, preferably 3.0 to 7.75 nm. In some embodiments, the porous silicate and/or aluminosilicate matrix is particles of MCM-41 and the nanocarrier has a mean pore size of 2 to 4 nm, preferably 2.25 to 3.75 m, preferably 2.5 to 3.5 nm, preferably 2.75 to 3.25 nm, preferably 2.9 to 3.1 nm, preferably 3 nm. In some embodiments, the porous silicate and/or aluminosilicate matrix is particles of KIT-6 and the nanocarrier has a mean pore size of 5 to 10 nm, preferably 5.25 to 9.75 nm, preferably 5.5 to 9.5 am, preferably 6 to 9 nm, preferably 6.25 to 8.75 nm, preferably 6.5 to 8.5 nm, preferably 6.75 to 8.25 nm, preferably 7 to 8 nm, preferably 7.25 to 7.75 nm, preferably 7.5 to 7.65 nm.

In some embodiments, the nanocarrier has a mean pore volume of 0.25 to 0.85 $cm^3/g$, preferably 0.30 to 0.75 $cm^3/g$, preferably 0.35 to 0.70 $cm^{3}$'/g, preferably 0.40 to 0.65 $cm^3/g$, preferably 0.44 to 0.64 $cm^3/g$. In some embodiments, the porous silicate and/or aluminosilicate matrix is particles of MCM-41 and the nanocarrier has a mean pore volume of 0.25 to 0.65 $cm^3/g$, preferably 0.30 to 0.60 $cm^3/g$, preferably 0.35 to 0.55 $cm^3/g$, preferably 0.40 to 0.50 $cm^3/g$, preferably 0.425 to 0.475 $cm^3/g$, preferably 0.44 $cm^3/g$. In some embodiments, the silicate and/or aluminosilicate matrix is particles of KIT-6 and the nanocarrier has a mean pore volume of 0.45 to 0.85 $cm^3/g$, 0.50 to 0.80 $cm^3/g$, preferably 0.55 to 0.75 $cm^3/g$, preferably 0.60 to 0.70 $cm^3/g$, preferably 0.625 to 0.675 $cm^3/g$, preferably 0.64 $cm^3/g$.

In general, the antioxidant may be any suitable antioxidant known to one of ordinary skill in the art. Examples of such antioxidants include, but are not limited to curcumin (and curcumin derivatives known as curcuminoids), Coenzyme Q10, quercetin, rutin, ascorbic acid, gallic acid, edaravone, N-acetylcysteine, alfa-lipoic acid, diosmin, hesperidin, oxerutins, baicalein, tocotrienols, resveratrol or other stilbenoids such as pterostilbene, retinoids and carotenes including Vitamin A, beta carotene, and alpha-carotene, astaxanthin, canthaxanthin, lutein, lycopene, and zeaxanthin, natural phenols including flavonoids, silymarin, xanthones, eugenol, phenolic acids, lipoic acid, acetylcysteine, uric acid, glutathione, and catechin. In some embodiments, the antioxidant is at least one selected from the group consisting of quercetin, rutin, coenzyme Q10, gallic acid, and curcumin.

Quercetin has the following chemical structure:

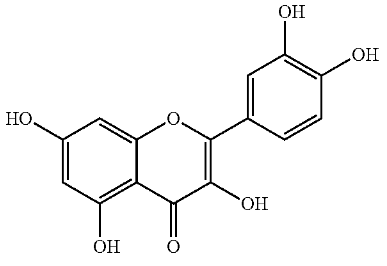 [SMILES: O=c1c(O)c(-c2ccc(O)c(O)c2)oc2cc(O)cc(O)c12]

Quercetin is a plant flavonol from the flavonoid group. It is found in a wide variety of food sources, but has very low water solubility and bioavailability. Inclusion of quercetin in the nanomedicinal composition of the present invention may overcome these disadvantageous properties of quercetin to increase an amount of quercetin which is delivered. Quercetin may be present in a crystalline or amorphous form or in a mixture of both crystalline and amorphous forms, for example at a ratio of 1-99 wt. %:99-1 wt. %, 10-90 wt. %:90-10 wt. %; 20-80 wt. %:80-20 wt. %, 30-70 wt. %:70-30 wt. %, 40-60 wt. %:60-40 wt. % or about 50 wt. %:about 50 wt. % (or any intermediate ratio of crystalline: amorphous forms).

Rutin has the following structure:

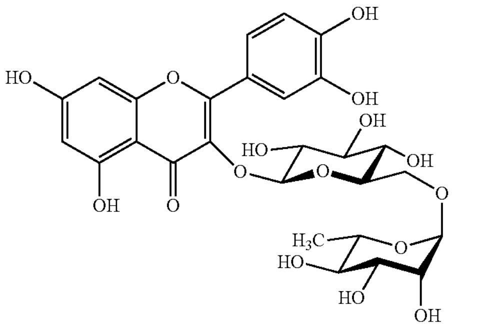

Rutin is the glycoside combining the flavonol quercetin and the disaccharide rutinose (α-L-rhamnopyranosyl-(1→6)-β-D-glucopyranose). Rutin may be present in a crystalline or amorphous form or in a mixture of both crystalline and amorphous forms, for example at a ratio of 1-99,wt. %: 99-1 wt. %, 10-90,wt. %: 90-10 wt. %; 20-80 wt. %: 80-20 wt. %, 30-70 wt. %: 70-30 wt. %, 40-60 wt. %: 60-40 wt. % or about 50 wt. %:about 50 wt. % (or any intermediate ratio of crystalline:amorphous forms).

Coenzyme Q10 (CoQ10) conforms to the following chemical structure:

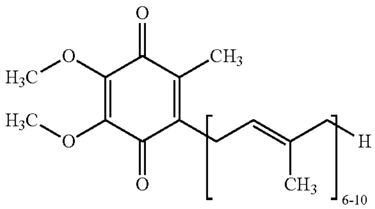

CoQ10 is a 1,4-benzoquinone, where Q refers to the quinone chemical group and 10 refers to the number of isoprenyl chemical subunits in its tail. Other forms of Coenzyme Q may be distinguished from CoQ10 by their number of isoprenyl subunits. A CoQ such as CoQ10 may be present in a crystalline or amorphous form or in a mixture of both crystalline and amorphous forms, for example at a ratio of 1-99 wt. %: 99-1 wt. %, 10-90 wt. %: 90-10 wt. %; 20-80 wt. %: 80-20 wt. %, 30-70 wt. %: 70-30 wt. %, 40-60 wt. %: 60-40 wt. % or about 50 wt. %:about 50 wt. % (or any intermediate ratio of crystalline:amorphous forms).

Gallic acid has the following structure:

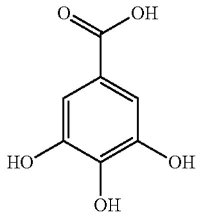 [SMILES: O=C(O)c1cc(O)c(O)c(O)c1]

Gallic acid is a potent antioxidant against cancers (leukemia, colon and lung cancer cells) and other metabolic disorders. Gallic acid may be present in a crystalline or amorphous form or in a mixture of both crystalline and amorphous forms, for example at a ratio of 1-99 wt. %: 99-1 wt. %, 10-90 wt. %: 90-10 wt. %; 20-80 wt. %: 80-20 wt. %, 30-70 wt. %: 70-30 wt. %, 40-60 wt. %: 60-40 wt. % or about 50 wt. %:about 50 wt. % (or any intermediate ratio of crystalline:amorphous forms).

Curcumin has the following structure:

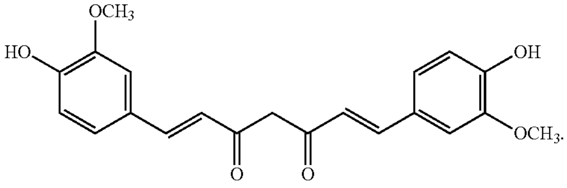 [SMILES: COc1cc(/C=C/C(=O)CC(=O)/C=C/c2ccc(O)c(OC)c2)ccc1O]

A curcuminoid is a linear diarylheptanoid. This class of compounds includes curcumin in both its keto and enolate forms as well as curcumin derivatives such as demethoxycurcumin and bisdemethoxycurcumin and their geometrical isomers and metabolites including sulfate conjugates and glucoronides. Other examples of curcumin derivatives or analogs include those described by Raja, el al., U.S. Pat. No. 9,447,023 B2, Raja, et a., U.S. Pat. No. 9,650,404 B2, Johnson, el al., U.S. Pat. No. 9,556,105 B2 or Vander Jagt, el at, U.S. Pat. No. 9,187,397 B2 (all incorporated by reference); especially for their descriptions of curcuminoid formulas and various chemical species of curcuminoids. In some embodiments of the invention curcumin or another curcuminoid may be included as an antioxidant in the nanomedicinal composition of the present disclosure.

Mixtures of curcuminoids are also contemplated such as one isolated from rhizomes of turmeric comprised of Curcumin (75-81%), Demethoxycurcumin (15-19%) and Bisdemethoxycurcumin (2.5-4.5%). The content of any one of a curcuminoid in a mixture may range from about 0 to about 100 wt. %, for example, 10-90 wt. %, 20-80 wt. %, 30-70 wt. %, 40-60 wt %., 50 wt. %, 40 wt. %, 33.3 wt. %, 30 wt. %, 20 wt. %, 10 wt. % or 5 wt % or 1 wt. %. A mixture may contain two, three or more different curcuminoids.

Curcumin may be present in a crystalline or amorphous form or in a mixture of both crystalline and amorphous forms, for example at a ratio of 1-99 wt. %: 99-1 wt. %, 10-9) wt. %: 90-10 wt. %; 20-80 wt. %: 80-20 wt. %, 30-70 wt. %: 70-30 wt. %, 40-60 wt. %: 60-40 wt. % or about 50 wt. %:about 50 wt. % (or any intermediate ratio of crystalline:amorphous forms). In some embodiments disclosed herein, curcumin will be in an amorphous form to increase its solubility.

Curcumin and its derivatives are known for their antimicrobial, anti-oxidative, anti-inflammatory, and anti-cancer properties such as malignancies in the brain or nervous system. Curcumin has also been proposed as an agent to treat oxidative stress, such as oxidative stress in the brain, and for treatment of neurodegenerative disease like Alzheimer's disease ("AD") or Parkinson's disease ("PD"); Lee, el al., Curr. Neuropharmacol. 2013 July; 11(4):338-378

INCORPORATED BY REFERENCE

Curcumin may also be functionalized or prepared as a conjugate with another moiety to modify or improve its pharmacokinetic properties. For example, curcumin can be adsorbed through functionalization to a silane, carboxylic acid, or biotin. Biocompatibility of a curcuminoid/hierarchical aluminosilicate can be increased by the modification with chitosan, or poly (D,L-lactide-co-glycolide), or polyethylene glycol.

In some embodiments, the antioxidant is curcumin.

Resveratrol has the following structure:

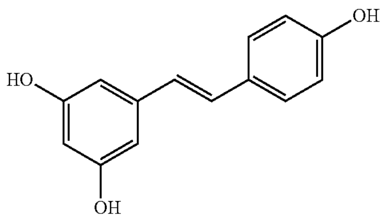 [SMILES: Oc1ccc(/C=C/c2cc(O)cc(O)c2)cc1]

Resveratrol is an antioxidant which belongs to the class of compounds known as stillbenoids, which are hydroxylated derivatives of stilbene (also known as 1,2-diphenylethene). The resveratrol may be resveratrol itself, or and a geometrical isomer or metabolite, including sulfate conjugates and glucoronides, of resveratrol. Resveratrol may be present in a crystalline or amorphous form or in a mixture of both crystalline and amorphous forms, for example at a ratio of 1-99 wt. %: 99-1 wt. %, 10-9) wt. %: 90-10 wt. %; 20-80 wt. %: 80-20 wt. %, 30-70 wt. %: 70-30 wt. %, 40-60 wt. %: 60-40 wt. % or about 50 wt. %:about 50 wt. % (or any intermediate ratio of crystalline:amorphous forms). The resveratrol may be present as the trans isomer depicted above, a cis isomer, or in a mixture of both the cis and trans isomers, for example at a ratio of 1-99 wt. %: 99-1 wt. %, 10-90 wt. %: 90-10 wt. %; 20-80 wt. %: 80-20 wt. %, 30-70 wt. %: 70-30 wt. %, 40-60 wt. %: 60-40,wt. % or about 50 wt. %:about 50 wt. % (or any intermediate ratio of cis:trans forms).

In some embodiments, the antioxidant is resveratrol.

In some embodiments, the antioxidant is present in the nanomedicinal composition in an amount of 5 to 50 wt %, preferably 10 to 47.5 wt %, preferably 15 to 45 wt %, preferably 17.5 to 42.5 wt %, preferably 20 to 40 wt %, preferably 22.5 to 37.5 wt %, preferably 25 to 35 wt %, preferably 26 to 34 wt %, preferably 27 to 33 wt %, preferably 28 to 31 wt %, preferably 29 to 30 wt %, based on a total weight of nanomedicinal composition.

In some embodiments, the antioxidant or its constituent compounds may interact with the surface of the nanocarrier via any suitable interaction known to one of ordinary skill in the art. Such interactions may be, for example physisorption (e.g. Van der Waals interactions), ion-ion interactions, ion-dipole interactions, dipole-dipole interactions, and hydrogen bonding. Such interaction may be through or involving appropriate functional groups on the antioxidant. Examples of such functional groups include, but are not limited to oxygen-containing functional groups such as alcohols, alkoxides, carboxylic acids and carboxylates, esters, ketones, and ethers; nitrogen-containing functional groups such as amines, amides, azides, diimides, imines, porphyrins, imides, isonitriles, nitriles, and nitro functional groups; phosphorous-containing functional groups such as phosphines, phosphites, phosphates, phosphonites, phosphonates, phosphinites, and phosphinates; and sulfur-containing functional groups such as thiols, thiolates, disulfides, sulfones, sulfonic acids and sulfonates, sulfoxides, thials, thioesters, thiosulfinates, thiocarboxylic acids and thiocarboxylates, sulfinic acids and sulfnates, thiocyanates, and isothiocyanates. The antioxidant may be electrically neutral or may have a charge, the charge being either positive or negative. A compound which is electrically neural may be devoid of charges or may have a combination of positive and negative charges in equal number so as to balance to electrically neutral (e.g. zwitterionic). A compound which is electrically neutral may interact to an equal extent with or be disposed equally upon both the interior and exterior surfaces of the nanocarrier. Alternatively, a compound which is electrically neutral may preferentially interact with either the interior or exterior surface of the nanocarrier. A compound which bears a positive charge may preferentially interact with or be disposed upon the exterior surface of the nanocarrier which bears a negative charge. A compound which bears a negative charge may preferentially interact with or be disposed upon the interior surface of the nanocarrier which bears a positive charge.

In some embodiments, the nanomedicinal composition comprises a biocompatible coating. Such a biocompatible coating may be disposed upon the nanocarrier and/or the antioxidant. In general, the biocompatible coating may be any suitable coating known to one of ordinary skill in the art. Examples of such suitable biocompatible coatings include, but are not limited to, agarose, agar, carrageen, alginic acid, alginate, an alginic acid derivative, a hyaluronate derivative, a polyanionic polysaccharide, chitin, chitosan, fibrin, a polyglycolide, a polylactide, a polycaprolactone, a dextran or copolymer thereof, polyvinyl pyrrolidone, a polyacrylate, a wax, a polyethylene-polyoxypropylene-block polymer, wool fat, poly(L-lactic acid), poly(DL-Lactic acid) copoly (lactic/glycolic acid), cellulose, a cellulose derivative, a glycol, polylactide-polyglycolide, polymethyldisiloxane, polycaprolactone, polylactic acid, and ethylene vinyl acetate.

In some embodiments, the antioxidant is curcumin and the nanomedicinal composition releases greater than 20%, preferably greater than 20.5%, preferably greater than 21%, preferably greater than 21.5%, preferably greater than 22%, preferably greater than 22.5%, preferably greater than 23%, preferably greater than 23.5%, preferably greater than 24%, preferably greater than 24.5%, preferably greater than 25% of a total weight of curcumin within 24 to 72 hours, preferably 27 to 69 hours, preferably 30 to 66 hours, preferably 33 to 63 hours, preferably 36 to 60 hours, preferably 39 to 57 hours, preferably 42 to 54 hours of contact with a suitable biological medium. In some embodiments, antioxidant is resveratrol the nanomedicinal composition releases greater than 7.5%, preferably greater than 8%, preferably greater than 8.5%, preferably greater than 9%, preferably greater than 9.5%, preferably greater than 10%, preferably greater than 10.5%, preferably greater than 11%, preferably greater than 11.5%, preferably greater than 12%, preferably greater than 12.5% of a total weight of resveratrol within 24 to 72 hours, preferably 27 to 69 hours, preferably 30 to 66 hours, preferably 33 to 63 hours, preferably 36 to 60 hours, preferably 39 to 57 hours, preferably 42 to 54 hours of contact with a suitable biological medium. Examples of suitable biological media include, but are not limited to, buffered saline solutions such as phosphate buffered saline, cell culture media such as Minimum Essential Medium (MEM, also known as Eagle's minimal essential medium EMEM), Dulbecco's Modified Eagle's Medium (DMEM), Iscove's Modified Dulbecco's Medium (IMDM), RPMI-1640, Ham's F-10, and F-12; animal tissue, or a subject's body.

In this aspect of the invention the release of the antioxidant may be due over a release period of at least 2 hours, preferably at least 4 hours, preferably at least 6 hours, preferably at least 8 hours, preferably at least 10 hours, preferably at least 12 hours, preferably at least 14 hours, preferably at least 16 hours, preferably at least 18 hours, preferably at least 20 hours Initial release rates are preferably 10-20 wt % of the total amount of antioxidant in the nanomedicinal composition during the induction period. Upon passage of the induction period and arrival of the nanomedicinal composition at a target site, a major portion of the antioxidant is released. In some embodiments, the major portion comprises at least 25 wt %, preferably at least 30 wt %, preferably at least 35 wt %, preferably at least 40 wt %, preferably at least 45 wt %, preferably at least 50 wt % of a total amount of antioxidant released.

In some embodiments, the induction period is provided by a coating disposed on the nanomedicinal composition, the coating as described above. In such embodiments, the coating may inhibit the release of the antioxidant. Removal of the coating by any suitable process, for example by dissolving, degrading, or digesting, may allow the pharmaceutical gent mixture to be released.

In some embodiments, the nanomedicinal composition has an antioxidant release rate of 0.1 to 10 wt % per hour, preferably 0.25 to 9 wt % per hour, preferably 0.5 to 7.5 wt % per hour, preferably 0.75 to 5 wt % per hour, preferably 1 to 4 wt % per hour based on a total initial weight of antioxidant. In such embodiments, the antioxidant release rate may be an average antioxidant release rate measured over the release period as described above. In some embodiments, the nanomedicinal composition has an initial antioxidant release rate which is maintained over an initial release period. In such embodiments, the initial release period may be followed by a second release period which has a second antioxidant release rate. The initial antioxidant release rate and/or second antioxidant release rate may be average release rates as described above. In some embodiments, the initial release period comprises the first 20 hours of release, preferably the first 18 hours of release, preferably the first 16 hours of release, preferably the first 14 hours of release, preferably the first 12 hours of release, preferably the first 10 hours of release. Such "first hours of release" are preferably measured from the initiation of release. The initiation of release may be measured by, for example a delivery of the nanomedicinal composition to a tumor site or a pre-determined amount of time after administration. Such a pre-determined time may be any suitable amount of time known to one of ordinary skill in the art, for example, an expected time for delivery of the nanomedicinal composition to the tumor site, an expected circulation time, an expected coating degradation time, or the like.

In some embodiments, the nanomedicinal composition reduces the viability of *Blastocystis* organisms by at least 75%, preferably by at least 77.5%, preferably at least 80%, preferably at least 82.5%, preferably at least 85%, preferably at least 87.5%, preferably at least 90%, preferably at least 92.5%, preferably at least 95%, preferably at least 97.5%, preferably at least 99% when the nanomedicinal composition is present for 24 hours in an amount of 100 to 1000 μg/mL.

The present disclosure also relates to a method of forming the nanomedicinal composition, the method comprising mixing the metal organic framework and the porous silicate and/or aluminosilicate matrix to form the nanocarrier, combining the nanocarrier and the antioxidant in an impregnation solution thereby forming the nanomedicinal composition, and isolating the nanomedicinal composition.

In general, the metal organic framework and the porous silicate and/or aluminosilicate matrix may be mixed using any suitable technique or equipment known to one of ordinary skill in the art. The metal organic framework and the porous silicate and/or aluminosilicate matrix can be present as particles as described above. In some embodiments, the metal organic framework and the porous silicate and/or aluminosilicate matrix are mixed as solids. That is, the mixing occurs between dry (i.e. without solvent) powders of the metal organic framework and the porous silicate and/or aluminosilicate matrix. In some embodiments, the mixing occurs as a slurry, a suspension, a dispersion, or other suitable wet (i.e. with solvent) form. In general, the solvent may be water, an aqueous solution, an organic solvent, or a mixture thereof. The aqueous solution may comprise, for example, a surfactant, a coating material as described above, a surface functionalization material as described above, a salt, or mixtures thereof. The organic solvent may be any suitable organic solvent, examples of which include, but are not limited to alcohols such as methanol, ethanol, n-propanol, 2-propanol (also known as isopropanol), ethylene glycol, diethylene glycol, and glycerol; hydrocarbons such as pentane, hexane, and heptane; ketones such as acetone and methyl ethyl ketone; esters such as ethyl acetate; amides such as dimethylformamide; ethers such as tetrahydrofuran, diglyme, and diethyl ether; nitriles such as acetonitrile; halogenated organic solvents such as methylene chloride (also known as dichloromethane), carbon tetrachloride, and chloroform; aromatic organic solvents such as benzene and xylene; amines such as trimethylamine and pyridine; and mixtures thereof.

In some embodiments, the mixing comprises ultrasonication. Such ultrasonication may occur in a dry powder as described above or in a slurry, a suspension, a dispersion, or other suitable wet form as described above.

In some embodiments, the impregnation solution comprises an alcohol having 1 to 5 carbon atoms. In some embodiments, the alcohol having 1 to 5 carbon atoms is methanol. In some embodiments, the impregnation solution comprises water. In some embodiments, the impregnation solution comprises glycerol. In some embodiments, the antioxidant is present in an amount of 0.5 to 3 mg/mL, preferably 0.75 to 2.5 mg/mL, preferably 1.0 to 2.25 mg/mL preferably 1.25 to 2.0 mg/mL, preferably 1.5 to 1.75 mg/mL, preferably 1.6 to 1.7 mg/mL of impregnation solution.

The present disclosure also relates to a method for method for treating an infection by a parasite in the genus *Blastocystis* in a subject, the method comprising administering to a subject in need of therapy a pharmaceutical composition comprising the nanomedicinal composition. *Blastocystis* is a genus of single-celled heterokont parasites, some species of which are capable of causing infection in a variety of animals, including mammals, birds, rodents, reptiles, amphibians, fish, and insects. Typically, infections occur in the gastrointestinal tract. *Blastocystis* has various morphological forms. Four commonly described forms are the vacuolar (otherwise known as central body), granular, amoeboid, and cyst forms. An infection treated by the present invention may involve any of these forms. Infection with a *Blastocystis* parasite can be referred to as "Blastocystosis".

The pharmaceutical composition may further comprise one or more pharmaceutically acceptable excipients.

As used herein, a "pharmaceutically acceptable excipient" refers to a carrier, adjuvant, vehicle, diluent, or other inert substance useful to further facilitate administration of a compound that does not cause significant irritation to an organism, does not abrogate the biological activity and properties of the administered active ingredient, and/or does not interact in a deleterious manner with the other components of the composition in which it contains. The term "carrier" encompasses any excipient, binder, diluent, filler, salt, buffer, solubilizer, lipid, stabilizer, or other material well-known in the art for use in pharmaceutical formulations. The choice of a carrier for use in a pharmaceutical composition will depend upon the intended route of administration for the pharmaceutical composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) peptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, Inc.; Bridgewater, N.J.), polyethylene glycol (PEG), and PLURONICS™ (BASF; Florham Park, N.J.). Examples of other inert substance added to a pharmaceutical composition to further facilitate administration of a compound, without limitation, include calcium carbonate, calcium phosphate, various sugars and types of starch, cellulose derivatives, gelatine, vegetable oils, and polyethylene glycols.

In some embodiments, the pharmaceutically acceptable excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate buffers, bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), C12-C16 fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphos-phazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the pharmaceutical composition may be in the form of solid dosage form such as tablets, caplets, capsules, powders, and granules, semi-solid dosage form such as gels, pastes, and suppositories, liquid dosage forms such as suspension, and dispersions, inhalation dosage form such as aerosols, sprays, and powders.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, suspensions, syrups, and elixirs containing inert diluents commonly used in the art, such as water. Such pharmaceutical compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection dispersions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These dispersions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable dispersion or suspension in a non-toxic parenterally acceptable diluent or solvent, for example, in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug. Such suppositories may be advantageous for treating colorectal infections, but may be unsuitable for treating other infection locations.

Administration by inhalation may be advantageous for treating lung infections, but may be unsuitable for treating other infection locations.

In other embodiments, the pharmaceutical composition comprising the nanomedicinal composition disclosed herein thereof has different release rates categorized as immediate release and controlled- or sustained-release.

As used herein, the terms "treat", "treatment", and "treating" in the context of the administration of a therapy to a subject in need thereof refers to the reduction or inhibition of the progression and/or duration of a disease (e.g. infection with a parasite in the genus *Blastocystis*), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of parasite in the genus *Blastocystis* cells before administration), or elimination of the parasite in the genus *Blastocystis* cells, (2) inhibiting parasite in the genus *Blastocystis* cell division and/or parasite in the genus *Blastocystis* cell proliferation, (3) relieving to some extent (or, preferably, eliminating) one or more symptoms associated with a pathology related to or caused in part by infection with a parasite in the genus *Blastocystis*, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic parasite in the genus *Blastocystis*, (8) a stabilization or reduction (e.g. by at least 10%, 20/s, 30%, 40%, 50%, 60%, 70%, preferably at least 80% relative to the initial growth rate) in the growth of cells of a parasite in the genus *Blastocystis*, (9) a reduction in mortality, (10) an increase in the response rate, the durability of response, or number of patients who respond or are in remission, (11) a decrease in the need for treatment by another therapeutic, and (12) preventing or reducing (e.g. by more than 10%, more than 30%, preferably by more than 60% of the population of cells of parasite in the genus *Blastocystis*.

The term "subject" and "patient" are used interchangeably. As used herein, they refer to any subject for whom or which therapy, including with the pharmaceutical compositions according to the present disclosure is desired. In most embodiments, the subject is a mammal, including but is not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), and rectal administration. Those of ordinary skill in the art are familiar with administration techniques that can be employed with the compounds and methods described herein. In preferred embodiments, the active ingredient and/or the pharmaceutical composition described herein are administered orally.

The dosage amount and treatment duration are dependent on factors, such as bioavailability of a drug, administration mode, toxicity of a drug, gender, age, lifestyle, body weight, the use of other drugs and dietary supplements, the infection stage or severity, tolerance and resistance of the body to the administered drug, etc., and then determined and adjusted accordingly. The terms "effective amount", "therapeutically effective amount", "pharmaceutically effective amount" or "sufficient amount" refer to that amount of the active ingredient being administered which will relieve to some extent one or more of the symptoms of the infection or disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In some embodiments, an effective amount is in the range of 0.1-30 g/kg of the nanomedicinal composition per body weight of the subject.

A treatment method may comprise administering the pharmaceutical composition of the current disclosure as a single dose or multiple individual divided doses, wherein the nanomedicinal composition is accumulated and releases the loaded antioxidant in or nearby the infected tissues. In some embodiments, the pharmaceutical composition is administered at various dosages (e.g. a first dose with an effective amount of nanomedicinal composition comprising 200 mg of the antioxidant per kilogram of the subject and a second dose with an effective amount of the nanomedicinal composition comprising 50 mg of the antioxidant per kilogram of the subject). In some embodiments, the interval of time between the administration of the pharmaceutical composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the pharmaceutical composition is administered once daily for at least 2 days, 5 days, 6 days, or 7 days. In certain embodiments, the pharmaceutical composition and one or more additional therapies are administered less than 1 day, 1 week, 2 weeks, 3 weeks, 4 weeks, 1 month, 2 months, 3 months, 6 months, 1 year, 2 years, or 5 years apart.

In some embodiments, the administration is stopped once the subject is treated.

The examples below are intended to further illustrate protocols for preparing, characterizing, and using the nanomedicinal composition or for treating an infection by a parasite in the genus *Blastocystis* using the nanomedicinal composition and are not intended to limit the scope of the claims.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

Examples

Nanocomposites

Bioactive naturally based polyphenols were nano-formulated, by accommodating ZIF-8, structured nano-mesosilica (MCM-41 or KIT-6) and natural antioxidants, curcumin or resveratrol. ZIF-8 with textural properties of 1040 $m^2/g$ (ZI200, sigma Aldrich), was purchased and used as a composite with mesoporous silica. The hexagonal shaped nano-silica (Si-MCM-41) and three-dimensional Si-KIT-6 was synthesized using hydrothermal technique. Cationic template cetyltrimethyl ammonium bromide (CTAB) and non-ionic template (P123) were used respectively to generate hexagonal and cubic pores for MCM-41 and KIT-6.

Synthesis of MCM-41 and KIT-6

For synthesis of MCM-41: 10.6 g of sodium metasilicate (silica source) was taken and dissolved in 50 ml of distilled water and stirred vigorously for 1 h. After dissolution, the solution was added dropwise to 4.5 g of CTAB solution dissolved in 40 ml of distilled water. The mixture was further stirred for 2 h and then pH was adjusted to 10.5 using diluted sulphuric acid solution (4N). The sol solution in milky form was hydrothermally treated at 140 °C for 12-24 h.

For synthesis of KIT-6: 4 g of P123 was dissolved in acidic HCl solution (2 M) and allowed to stir for 1 h. Then 4 g of n-butanol (co-solvent) was added along with 8.6 g of tetraethylorthosilicate (silica source) and stirred for 24 h. The mixture in polypropylene bottle was transferred to oven and hydrothermally aged at 100 °C for 24 h. The precipitate was filtered, washed several times with excess water and dried at 100 °C for 12 h. The two samples (MCM-41 and KIT-6) were finally calcined at 550 °C for 6 h.

Preparation of Medicinal Nanocomposite

The calcined form of MCM-41 and KIT-6 was composited with ZIF-8 using ultrasonic technique forming ZIF-8/MCM-41 and ZIF-8/KIT-6 nanocomposite (ZIF-8/structured silica ratio of 0.105). In order to nano-formulate with bioactive polyphenol components, a rotary evaporator was used. In brief, curcumin or resveratrol(500 mg) were loaded over ZIF-8/MCM-41 and ZIF-8/KIT-6 (2000 mg) in methanolic solution (300 ml) and sonicated for 10 min. Then the solvent was evaporated using rotary evaporator technique to form MCM-41/ZIF-8/antioxidant and KIT-6/ZIF-8/antioxidant nanocomposites. The formulated nanocomposites were characterized using phase (XRD), textural features (BET), chemical coordination environment of metal species (DRS-UV-visible), active component functionalization (FTIR) and transmission electron microscopy (JEM2100F from JEOL).

Drug Release Study

The release trend of antioxidants (resveratrol and curcumin) were investigated using four different nanoformulations MCM-41/ZIF-8/Curcumin, KIT-6/ZIF-8/Curcumin, MCM-41/ZIF-8/Resveratrol and KIT-6/ZIF-8/Resveratrol nanocomposites. Prior to the study, the dialysis membrane (12 KDa, Sigma Aldrich) was activated and then 15 mg of nanoformulation was dispersed in 25 ml of PBS solution (pH 5.6 and 7.4). The release of antioxidants are studied at 37 °C. At regular time interval, 5 ml of solution was withdrawn, and release of antioxidants were measured using UV-visible spectroscopy. The withdrawn solution (5 ml) was replaced with equal volume of fresh PBS solution.

The release content was identified at specific wavelength of curcumin and resveratrol (307 nm). Prior to analysis, calibration curve for curcumin and resveratrol were established. At first, an initial stock solution was prepared with concentration of 1000 μg/ml for curcumin and resveratrol. Various concentration of aliquots 5, 10, 15, 20, 25 and 30 μg/ml was prepared with makeup volume to 10 ml using release medium PBS solution (pH=5.6 or 7.4) and calibration curve established against blank at maximum absorption wavelength λmax of 428 nm and 307 nm, respectively. Linear regression for curcumin and resveratrol were found to be y=0.0041x+0.0237 and y=0.0579x+0.0318, where y corresponds to absorbance and x to the concentration of antioxidant release (μg/ml). The correlation coefficient was of 0.9982 and 0.995 for maximum absorption for curcumin and resveratrol, respectively. The release study was repeated in triplicates.

*Blastocystis* Parasite

Suspensions of cultured *Blastocystis* from symptomatic patients were used for evaluating biological activities of the formulated nanocomposites. *Blastocystis* were obtained from the El-Badry Lab where ethically approved by the Deanship of Scientific Research and Postgraduate Studies of Imam Abdulrahman Bin Faisal University under the Institutional Review Board (IRB) number (IRB #2021-01-009).

*Blastocystis* were sub-cultured using fresh Jones' medium enriched with 10% horse serum according to Jones to get rid of stool debris [Jones, W. Ann Trop Med Parasitol., 1946, 40, 130-140; & Zman, V., and Khan, K. Southt Asian J Trop Med Public Health, 1994, 25, 792-793, each of which is incorporated herein by reference in its entirety]. Cultures with vacuolar forms of *Blastocystis* greater than $10^6$ were used for evaluating biological activities of the formulated nanocomposites.

Molecular Characterization of Isolated *Blastocystis*

One ml of subculture was suspended in 7 ml PBS, vortexed, centrifuged for 1 min at 12.000×g, then the pellet was kept for DNA extraction. DNA was extracted from pelleted *Blastocystis* cysts, using commercial DNA extraction kit (DNA MiniPrep™ kit, Zymo Research Corp., USA) following the kit's protocol. As per Stensvold's recommendations, *Blastocystis* DNA was amplified and genotyped using two PCR reactions, targeting *Blastocystis* specific SSU rDNA and subtype-specific Sequence-Tagged-Site (STS) in order to detect the seven standardized subtypes (STs 1-7)[Stensvold, C. R. J Clin Microbiol., 2003, 51, 190-194, incorporated herein by reference in its entirety]. PCR conditions and reactions were performed as mentioned by Yoshikawa et al. and Scicluna et al, [Yoshikawa, H., et. al., J Eukaryotic Microbiol., 2003, 50, 710-711; & Scicluna S M, et. al., Protist., 2006, 157, 77-85, each of which is incorporated herein by reference in its entirety].

In Vitro Challenging of *Blastocystis* with Nanocomposites

Suspension of cultured *Blastocystis* cysts, in logarithmic growth phase of $10^6$/ml, were inoculated in sets of culture tubes with Jones' culture media. Haemocytometer counting chamber was used to count the number of *Blastocystis* cysts. The experiments contained 3 groups as follows:

- Group 1 (G1): parasite (negative, not treated) control group, containing only cultured cysts of *Blastocystis.*
- Group 2 (G2): drug (positive) control, containing cultured parasites exposed to 500 μg/ml metronidazole as reference anti-*Blastocystis* therapy.
- Group 3 (G3): nanocomposites tested group, containing cultured parasites exposed to the three nanocomposites. G3 was further divided into subgroups to test three nanocomposites (G3A, G3B and G2C) at different concentrations (G3i-iv). Parasites were exposed to increasing concentrations of the three nanocomposites of 100 μg/ml (G3i) 200 μg/ml (G3ii), 500 μg/ml (G3iii) and 800 μg/ml (G3iv) (W/V). All tubes were incubated at 37 °C in humidified CO2 for 48 hours.

All tested nanocomposites for each concentration were prepared by diluting stock solution in appropriate amount of PBS. The volume of each of the experiment tubes was brought to 1 ml with *Blastocystis* $10^6$/ml concentration. All experiments were performed in triplicate [El-Sayed, S. H., et. al., Res J Parasitol., 2017, 12, 2, 3344; Méabed, E. M. H., Phytomedicine, 2018, 1, 43, 158-163; & Mokhtar, A. B., et. al., int J Environ Res Public Health, 2019, 16, 1555, each of which is incorporated herein by reference in its entirety].

Assessment of Anti-*Blastocystis* Activities of the Nanocomposites

The number of *Blastocystis* cysts from all cultured tubes included in the experiment were counted under the microscope in haemocytometer counting chamber, and cultured *Blastocystis* cysts were tested for their viability using Trypan blue solution (0.4%). Trypan blue is a vital stain which does not stain a live *Blastocystis* cysts, while it stain dead *Blastocystis* cysts blue. The dead *Blastocystis* cysts were further confirmed by microscopic detection of cell wall disruption and destruction of internal structures. All cultured tubes were examined for percentage of reduction in growth of *Blastocystis* cysts each hour for 5 hours then after 24 hours. The minimal lethal concentration (MLC) was determined to be the concentration at which no *Blastocystis* cysts were observed.

Statistical Analysis

The obtained data was statistically analyzed using SPSS software and presented as mean and standard deviation (SD). All the data shows the mean for each of the three independent experiments. Means were compared and variances were analyzed. P values of less than 0.05 indicate statistical significance.

Results

Figure 2:
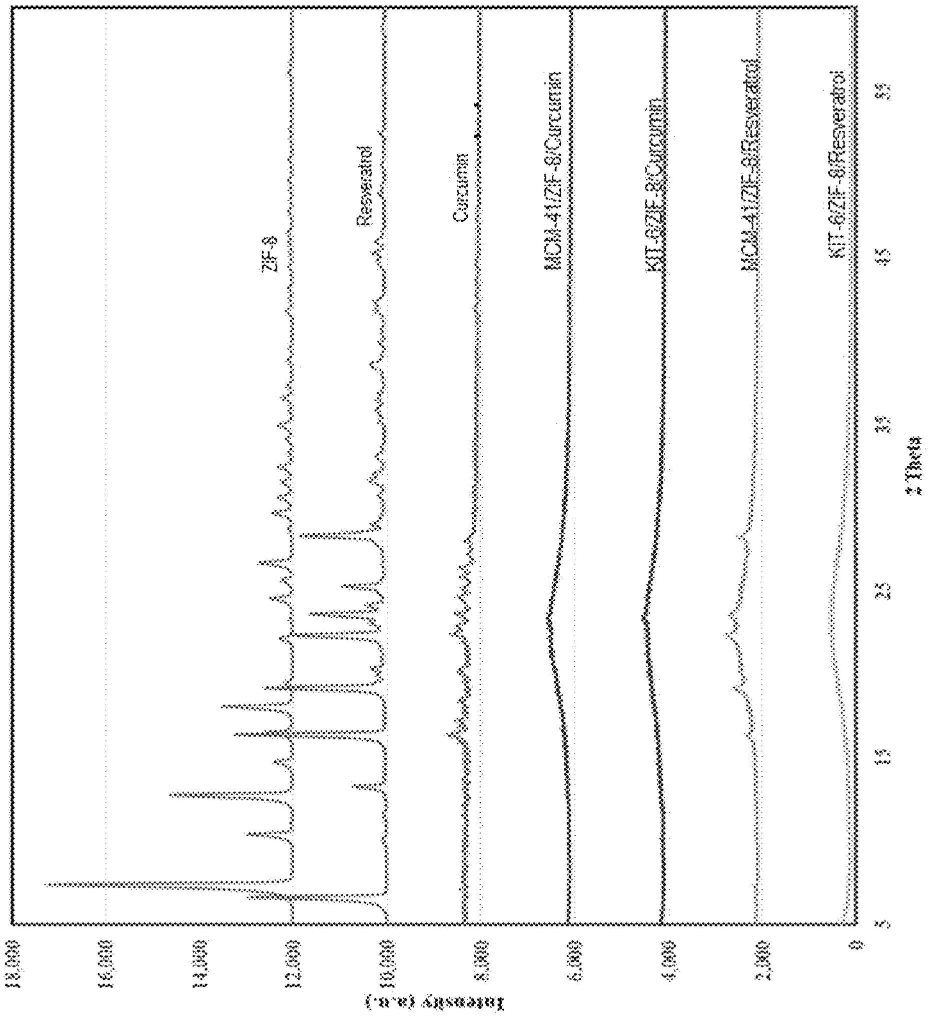
FIG. 2 shows X-ray diffraction pattern of ZIF-8, Resveratrol, Curcumin, MCM-41/ZIF-8/Curcumin, KIT-6/ZIF-8/Curcumin, MCM-41/ZIF-8/Resveratrol, and KIT-6/ZIF-8/Resveratrol nanocomposites.

MCM-41/ZIF-8/Curcumin, KIT-6/ZIF-8/Curcumin, MCM-41/ZIF-8/Resveratrol and KIT-6/ZIF-8/Resveratrol and Zn nanocomposites were synthesized. The XRD analysis of ZIF-8, Resveratrol, Curcumin, MCM-41/ZIF-8/Curcumin, KIT-6/ZIF-8/Curcumin, MCM-41/ZIF-8/Resveratrol and KIT-6/ZIF-8/Resveratrol nanocomposites are shown in FIG. 2.

ZIF-8 exhibited typical crystalline peaks corresponding to sodalite structure. Resveratrol and Curcumin indicated a characteristics crystalline peaks. Four samples of composites were analyzed to study the extent of amorphous transformation of bioactive components in contact with mesoporous silica. The characteristic peaks of ZIF-8 and curcumin were not observed in XRD spectra of MCM-41/ZIF-8/Curcumin and KIT-6/ZIF-8/Curcumin. These findings indicate the amorphous transformation of ZIF-8 and curcumin inside the hexagonal and cubic pores of MCM-41 and KIT-6, respectively. In case of MCM-41/ZIF-8/Resveratrol, some peaks of resveratrol were seen, while in cubic shaped KIT-6 none were observed. These results show that some crystalline forms of resveratrol were still present inside the hexagonal pores of MCM-41. Overall, the transformation of ZIF-8 and antioxidants from crystalline to amorphous form increased their bioavailability.

Figure 3A:
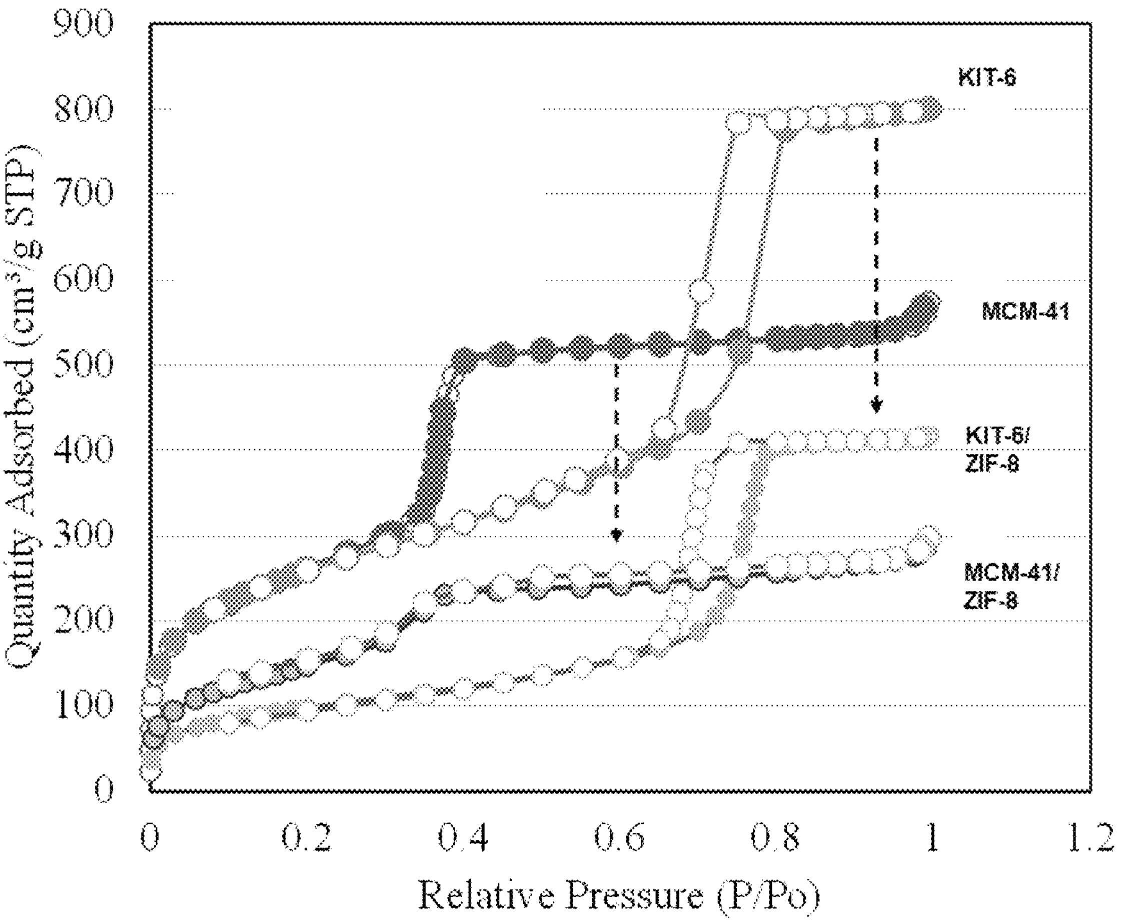
FIG. 3A shows nitrogen adsorption isotherms of MCM-41, MCM-41/ZIF-8, KIT-6, and KIT-6/ZIF-8.
Figure 3B:
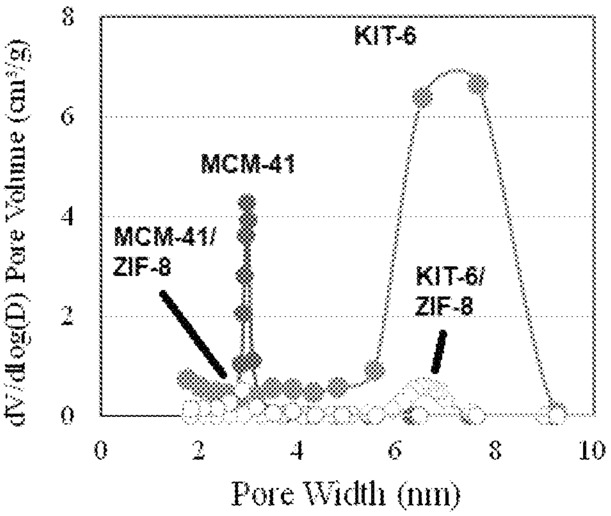
FIG. 3B shows a pore size distribution plot of MCM-41, MCM-41/ZIF-8, KIT-6, and KIT-6/ZIF-8.

The textural properties of MCM-41, KIT-6, MCM-41/ZIF-8 and KIT-6/ZIF-8 nanocomposites were measured using nitrogen adsorption technique (FIG. 3A). The surface area, pore volume and average pore size values are presented in Table 1. The adsorption-desorption isotherm pattern of MCM-41 and KIT-6 samples exhibited a typical type IV isotherm with capillary condensation due to large meso sized pores at 0.2-0.4 and 0.6-0.8, respectively. The surface area of MCM-41 and KIT-6 was 942 $m^2$/g and 897 m/g, respectively. However, the formation of nanocomposite with ZIF-8 reduced the surface area of MCM-41/ZIF-8 and KIT-6/ZIF-8 to 594 $m^2$/g and 336 $m^2$/g. The similar trend in the pore volume and pore size distribution shows the effective interaction of structured silica with ZIF-8 (FIG. 3B).

Figure 4A:
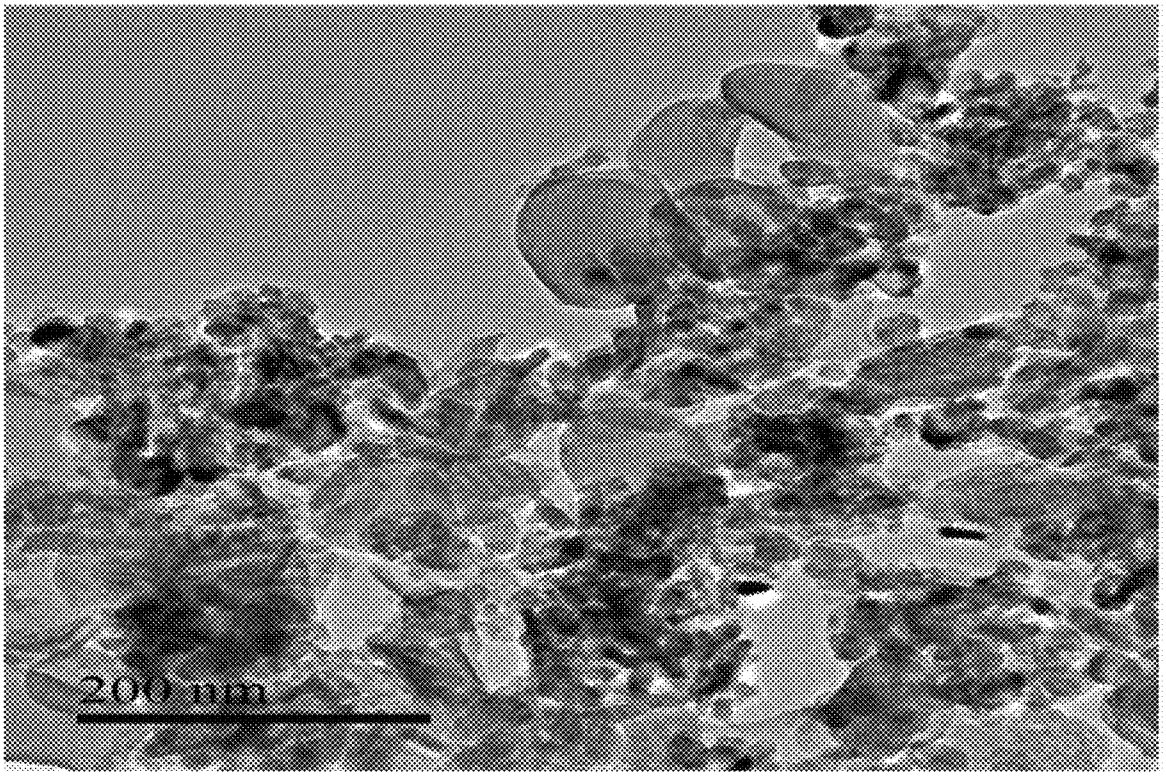
FIGS. 4A-4B show transmission electron microscope (TEM) images of KIT-6/ZIF-8 at magnification of 200 nm (FIG. 4A) and 20 nm (FIG. 4B).
Figure 4B:
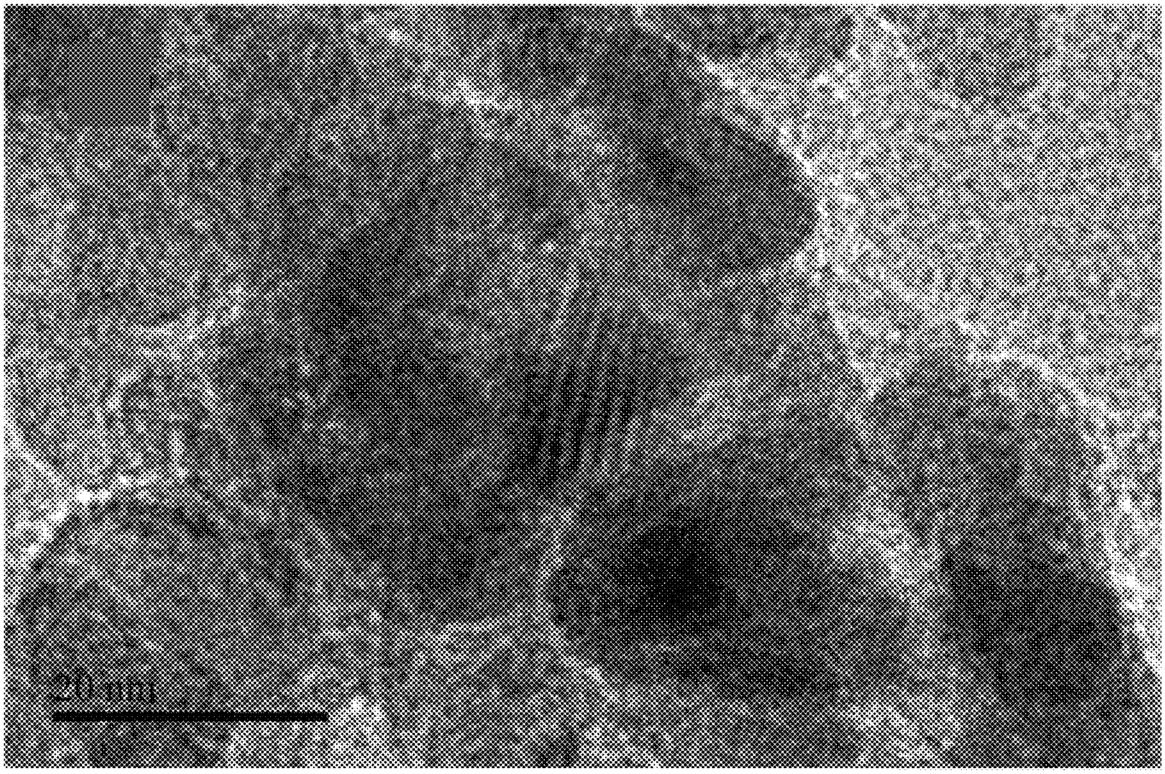

The morphological analysis of KIT-6/ZIF-8 using TEM clearly shows the nanocomposite formation between KIT-6 and ZIF-8. The sphere shaped ZIF-8 shown to be well distributed along with large surface of KIT-6 (FIGS. 4A-4B).

TABLE 1

| Textural and structural properties. | | | |
|---|---|---|---|
| Sample | BET surface area ($m^2$/g) | Pore volume ($cm^3$/g) | Average pore size (nm) |
| MCM-41 | 942 | 0.87 | 3.7 |
| KIT-6 | 897 | 1.24 | 5.5 |
| MCM-41/ZIF-8 | 594 | 0.44 | 3.0 |
| KIT-6/ZIF-8 | 336 | 0.64 | 7.6 |

Figure 5A:
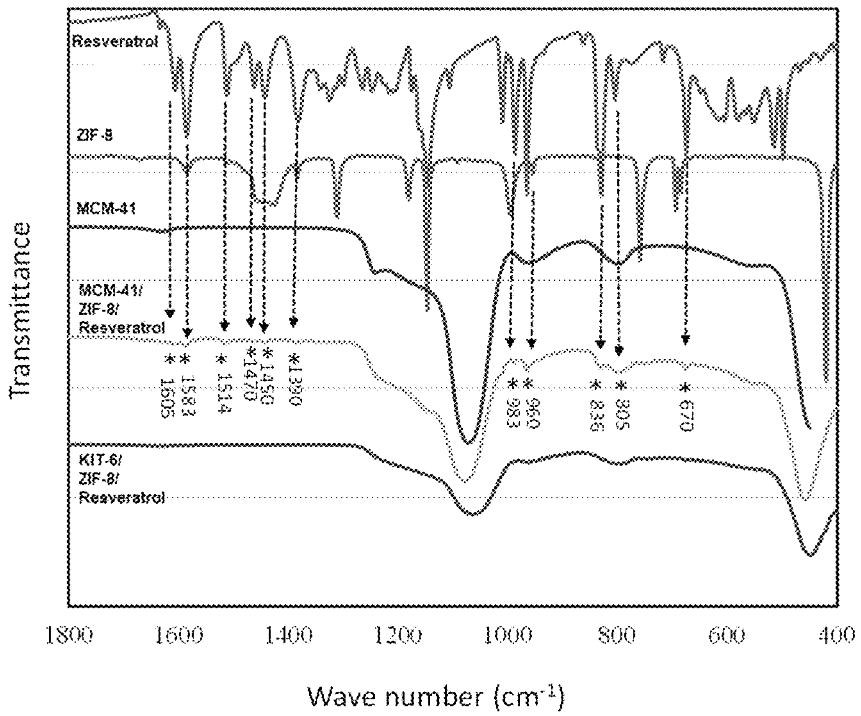
FIG. 5A shows the FTIR spectra of Resveratrol, ZIP-8, MCM-41, MCM-41/ZIF-8/Resveratrol, and KIT-6/ZIF-8/Resveratrol nanocomposites.
Figure 5B:
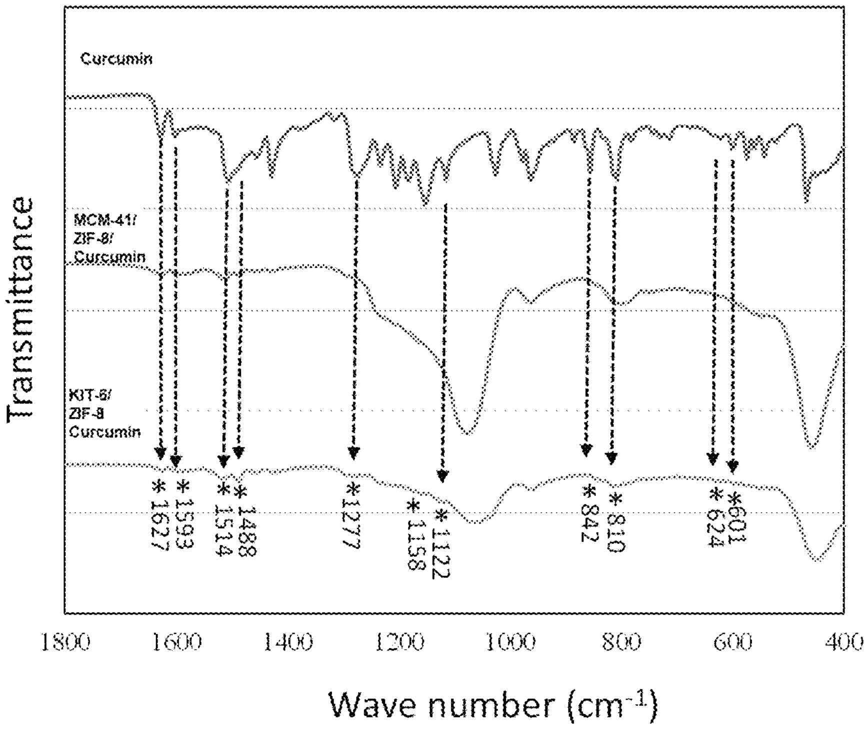
FIG. 5B shows the FTIR spectra of Curcumin, MCM-41/ZIF-8/Curcumin, and KIT-6/ZIF-8/Curcumin nanocomposites.

FIG. 5A shows the FTIR spectra of Resveratrol, ZIF-8, MCM-41, MCM-41/ZIF-8/Resveratrol and KIT-6/ZIF-8/Resveratrol nanocomposites. The spectra of resveratrol and ZIF-8 showed a characteristic band corresponding to carbon-carbon double bonds of aromatic compound at 1605, 1583 and 1514 $cm^{-1}$. Phenolic compound containing a carbonyl group showed a band at 1155 $cm^{-1}$. The hydroxyl group from the phenolic compound showed a stretching at 1390 $cm^{-1}$. The C—H group showed a band at 960 $cm^{-1}$, indicating the trans resveratrol configuration. The C—H vibration band of arene conjugated to olefinic group can be seen at 805 $cm^{-1}$ and 836 $cm^{-1}$. In the various bands that are observed between 650-500 $cm^{-1}$, a ═C—H of olefinic group can be seen at 670 $cm^{-1}$. Compared to functional bands of hexagonal pores of MCM-41, various functional peaks of resveratrol in reduced signals were observed, indicating the presence of amorphous components at the external pores, however, no such peaks of resveratrol were observed in the cubic shaped pores of KIT-6. This trend shows effective pore filling of nanosized resveratrol in cubic pores of KIT-6. FIG. 5B shows the FTIR spectra of curcumin, MCM-41/ZIF-8/Curcumin and KIT-6/ZIF-8/Curcumin nanocomposites. The functional groups of curcumin including >C═O and C═C were observed between 1627-1450 $cm^{-1}$. In particular, a characteristic enolic OH of curcumin can be observed at 962 $cm^{-1}$. The —C—O—C— chain vibrations (symmetric and asymmetric) can be observed between 1000-1450 $cm^{-1}$. In the case of both nanocomposites, the curcumin functional group showed a reduction in >C═O and C═C peaks. A reduction in hydroxyl peak of enol group also indicates an overall effective interaction of curcumin through enol and other functional groups. In the case of MCM-41 and KIT-6, the broadening of peak at about 1023 $cm^{-1}$ indicates the effective functionalization of curcumin in the hexagonal and cubic pores of nanocomposite.

Figure 6:
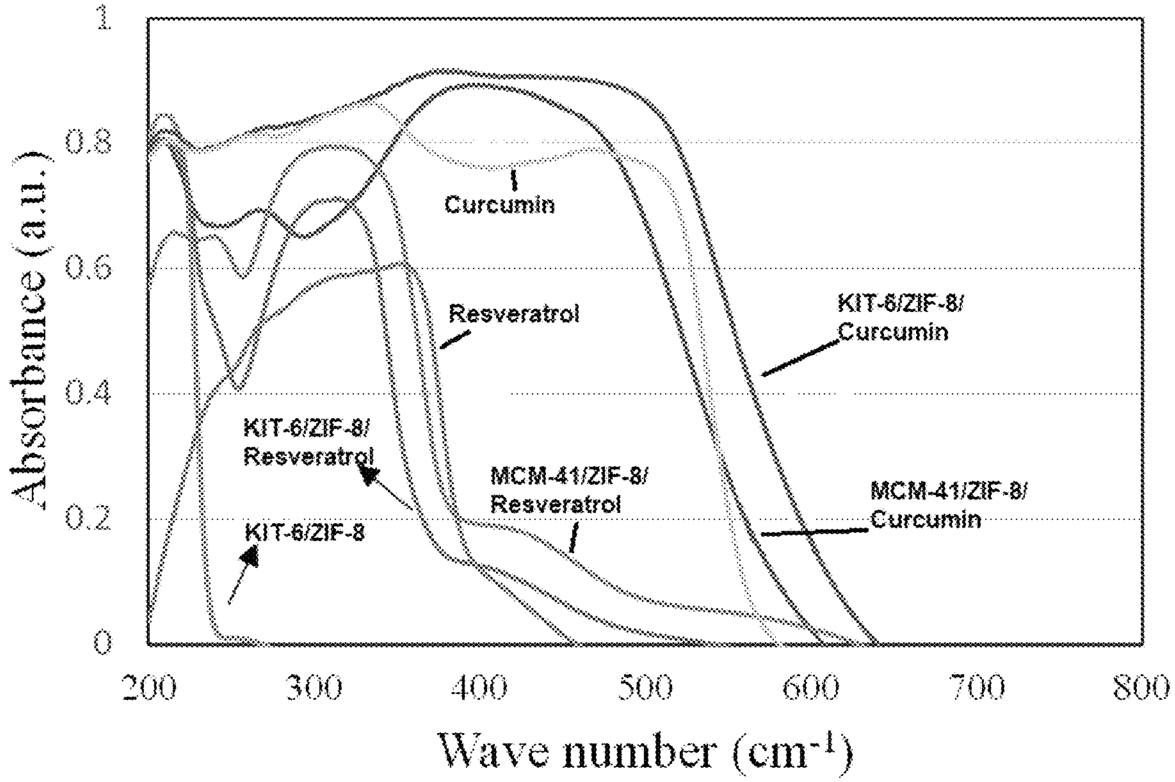
FIG. 6 shows the diffuse reflectance spectra of KIT-6/ZIF-8, Resveratrol, Curcumin, MCM-41/ZIF-8/Curcumin, KIT-6/ZIF-8/Curcumin, MCM-41/ZIF-8/Resveratrol, and KIT-6/ZIP-8/Resveratrol nanocomposites.

FIG. 6 shows the diffuse reflectance spectra of KIT-6/ZIF-8, Resveratrol, Curcumin, MCM-41/ZIF-8/Curcumin, KIT-6/ZIF-8/Curcumin, MCM-41/ZIF-8/Resveratrol and KIT-6/ZIF-8/Resveratrol nanocomposites. KIT-6/ZIF-8 shows a strong absorption at 212 nm, which can be ascribed to the presence of $Zn^{2+}$ species in ZIF-8. Resveratrol and curcumin revealed broad absorption between 200-600 nm. After loading of curcumin and resveratrol, the absorption maximum increases significantly over MCM-41/ZIF-8 and KIT-6/ZIF-8/nanocomposites. Such expansion behavior clearly indicates the composite formation over two supports.

Drug Delivery Study

Figure 7:
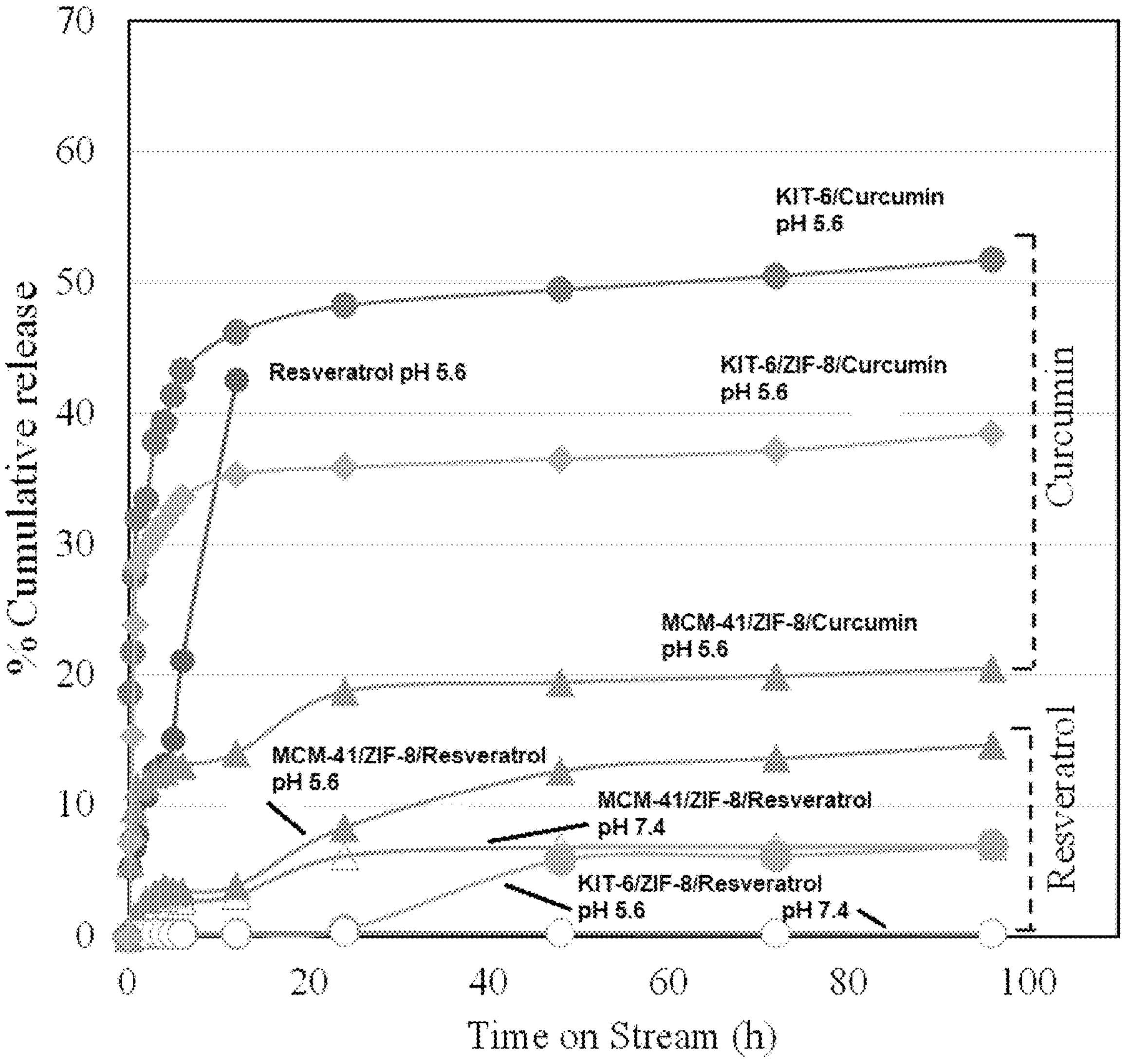
FIG. 7 shows the release profile of antioxidants loaded nanocomposites at 37 °C for % h Resveratrol (pH=5.6), MCM-41/ZIF-8/Resveratrol (pH=5.6), MCM-41/ZIF-8/Resveratrol (pH=7.4), KIT-6/ZIF-8/Resveratrol (pH=5.6), KIT-6/ZIF-8/Resveratrol (pH=7.4), KIT-6/Curcumin (pH=5.6), KIT-6/ZIF-8/Curcumin (pH=5.6), and MCM-41/ZIF-8/Curcumin (pH=5.6).

The drug release ability of antioxidants on MCM-41!ZIF-8!Curcumin, KIT-6!ZIF-8/Curcumin, MCM-41/ZIF-8/Resveratrol and KIT-6/ZIF-8/Resveratrol nanocomposites was studied at intestinal parasite pH condition for human intestine ranging pH 5.3 to 7.4 (FIG. 7). Resveratrol (pure form) was studied for comparative purpose. In the release study, as-such resveratrol in the absence of nanocarrier showed a burst release as expected and reached a maximum of 43% within 12 h. In case of nanocomposite/resveratrol release profiles, MCM-41/ZIF-8 exhibited a slow release of about 15% for 96 h, while KIT-6/ZIF-8 showed even a lower release profile of about 7% for 96 h. At neutral pH condition, both nanocomposites showed a reduced release of resveratrol. FIG. 7 shows the curcumin on KIT-6 support alone. A quick release of curcumin was observed reaching at about 37% within 3 h and then steadied and reached about 52% by 96 h. In case of nanocomposites, a wider difference was observed in curcumin release. KIT-6/ZIF-8 showed a high percentage of cumulative release of curcumin (39%) than MCM-41/ZIF-8 (21%) at pH 5.6. MOFs are shown to exhibit pH sensitive drug releases. Further, the degradation of MOF at acidic, neutral and basic conditions tends to influence the drug release characteristics. MOF based on zirconium has shown to exhibit pH sensitive release of biphosphate based drug alendronate. The nanocarrier showed high drug loading efficiency and pH sensitive release capability due to inherent anchoring nature of metal-oxygen clusters. The high release at acidic pH of 5.5 was mainly attributed to the protonation of drug leading to higher release than neutral pH of 7.4 [Zhu X, et. al., Chemical Communications, 2014, 50, 63, 8779-82; & Cai W, et. al., Advanced Science, 2019, 6, 1, 1801526, each of which is incorporated herein by reference in its entirety). The ZIF-8 nanocarrier with pH sensitivity has been reported to be beneficial against parasite protozoan *Trypanosoma* infection. At acidic pH of 4.5, a quick release of benzimidazole was observed, while the trend changes to a sustained and longer release at pH 7.4 (de Moura Ferraz, L. R., et. al., J Mater Sci: Mater Med. 2021, 32, 59, incorporated herein by reference in its entirety]. In the present nanocomposites, the hydroxyl functionalization of curcumin and resveratrol with nanocomposites could be critical in protonation and assist such release in acidic pH condition. Both MCM-41/ZIF-8 and KIT-6/ZIF-8 nanocomposites showed a reduction in surface area and hierarchical pore formations compared to MCM-41 and KIT-6 (FIG. 3B). In parallel, an intermediate pH sensitive release with steady modulation of antioxidants occurs in KIT-6/ZIF-8 than KIT-6 and resveratrol.

Anti-*Blastocystis* Activity

The anti-*Blastocystis* cysts activities of the nanocomposites, were determined by calculating the viability percent of *Blastocystis* cysts exposed to different increasing concentrations of all the nanocomposites each hour for 5 hours then after 24 hours (100, 200, 500 and 800 µg/ml). The parasite control group showed no effect on viability of *Blastocystis* cysts. There was a reduction in number of cysts exposed to the nanocomposite; the maximum effect was observed with Resveratrol/ZIF-8/MCM-41 (see Table 2).

Resveratrol/ZIF-8/MCM-41 showed the maximum percentage of *Blastocystis* cysts destruction (~100%) at concentration of 500 µg/ml after 5 hours of exposure as found using standard drug (metronidazole) with statistical significance.

Figure 8A:
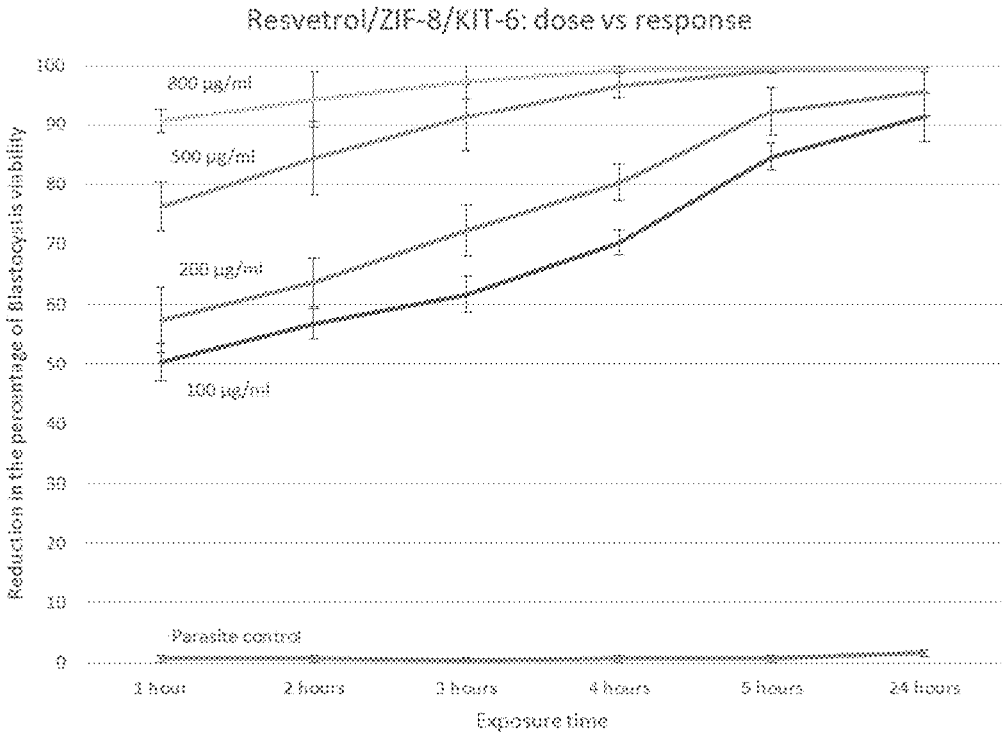
FIGS. 8A-8C show the reduction in the percentage of *Blastocystis* cysts viability after exposure to increasing concentrations of resveratrol/ZIF-8/Kit-6 nanocomposite (FIG. 8A), curcumin/ZIF-8/MCM-41 nanocomposite (FIG. 8B), and ZIF-8/KIT-6 nanocomposite (FIG. 8C).
Figure 8B:
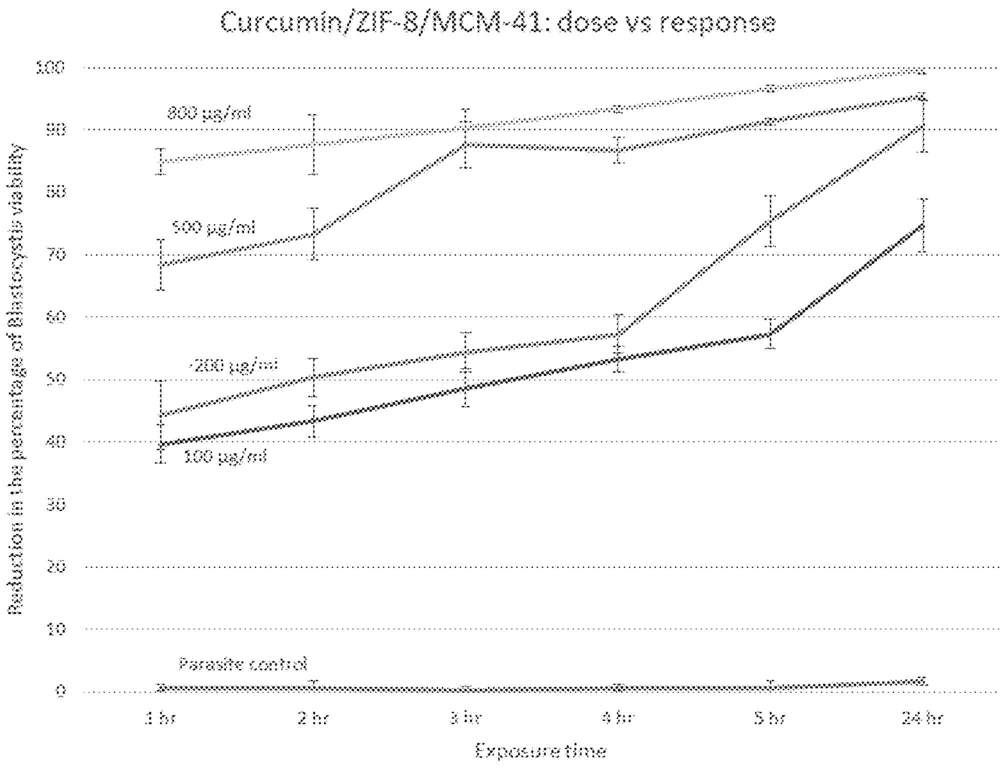
Figure 8C:
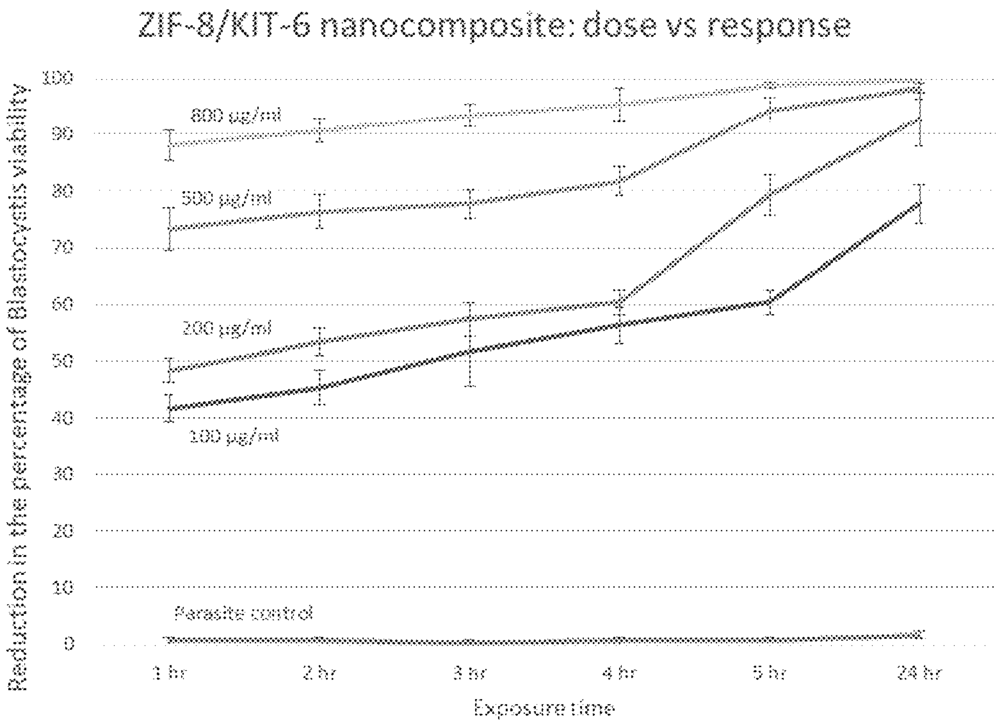

All of the Curcumin/ZIF-8/MCM-41 nanocomposites tested concentrations and three concentrations (200, 500 and 800 µg/ml) of the antioxidant-free nanocomposite killed more than 90% of the viable *Blastocystis* cysts in one day compared to parasite control, untreated *Blastocystis* cysts. The percentage of viability of *Blastocystis* cysts steadily declined over the experiment time; it was dose-dependent in all tested nanocomposites, with stronger effect using resveratrol, which was able to kill >90 of *Blastocystis* cysts in one hour (Table 2). There was a statistical significance in low doses of the nanocomposites (Table 2). The plots of these results are shown in FIGS. 8A-8C.

TABLE 2

Reduction in the percentage of viability of *Blastocystis* cysts in parasite control group (negative control), after exposure to metronidazole (positive control), and after exposure to the three nanocomposites.

| | | | Time of exposure /hour | | | | | |
|---|---|---|---|---|---|---|---|---|
| | | | 1 hour | 2 hours | 3 hours | 4 hours | 5 hours | 24 hours |
| Parasite control | | | 0.67 ± 0.58 | 0.67 ± 1.15 | 0.33 ± 0.58 | 0.67 ± 0.58 | 0.67 ± 1.15 | 1.67 ± 0.58 |
| Metronidazole control | | | 81.67 ± 2.52 | 87.67 ± 1.53 | 91.33 ± 1.53 | 96.33 ± 1.15 | 98.67 ± 0.58 | 99.33 ± 0.58 |
| Resvetrol/ZIF8/ KIT-6 | 100 µg/ml | Mean ± | 50.33 ± | 56.67 ± | 61.67 ± | 70.33 ± | 84.67 ± | 91.33 ± |
| | | Sd | 3.06 | 2.52 | 3.06 | 2.08 | 2.31 | 4.16 |
| | | P. value | 0.0004* | 0.0002* | 0.0005* | 0.0004* | 0.0003* | 0.0003* |
| | 200 µg/ml | Mean ± | 57.33 ± | 63.67 ± | 72.33 ± | 80.33 ± | 92.33 ± | 95.67 ± |
| | | Sd | 5.51 | 4.04 | 4.16 | 3.06 | 4.04 | 4.16 |
| | | P. value | 0.001* | 0.001* | 0.0007* | 0.0003* | 0.0003* | 0.004* |
| | 500 µg/ml | Mean ± | 76.33 ± | 84.33 ± | 91.33 ± | 96.67 ± | 99.33 ± | 99.67 ± |
| | | Sd | 4.04 | 6.11 | 5.68 | 2.08 | 0.58 | 0.58 |
| | | P. value | 0.0004* | 0.0006* | 0.0008* | 0.0001* | 0.04* | 0.05* |
| | 800 µg/ml | Mean ± | 90.67 ± | 94.33 ± | 97.33 ± | 99.33 ± | 99.67 ± | 99.67 ± |
| | | Sd | 2.08 | 4.73 | 2.89 | 0.58 | 0.58 | 0.58 |
| | | P. value | 0.008* | 0.0003* | 0.0001* | 0.21 | 0.42 | 0.12 |
| Curcumin/ZIF-8/ MCM-41 | 100 µg/ml | Mean ± | 39.67 ± | 43.34 ± | 48.67 ± | 53.34 ± | 57.34 ± | 74.67 ± |
| | | Sd | 2.3 | 3.05 | 6.03 | 3.21 | 2.08 | 3.51 |
| | | P. value | 0.0004* | 0.0002* | 0.0005* | 0.0004* | 0.0003* | 0.0003* |
| | 200 µg/ml | Mean ± | 44.34 ± | 50.34 ± | 54.34 ± | 75.34 ± | 84.34 ± | 90.67 ± |
| | | Sd | 2.08 | 2.52 | 3.06 | 2.08 | 3.51 | 4.73 |
| | | P. value | 0.001* | 0.001* | 0.0007* | 0.0003* | 0.0003* | 0.001* |
| | 500 µg/ml | Mean ± | 68.34 ± | 73.34 ± | 78.34 ± | 86.67 ± | 91.33 ± | 95.34 ± |
| | | Sd | 3.79 | 3.06 | 2.52 | 2.52 | 2.08 | 2.08 |
| | | P. value | 0.0004* | 0.0006* | 0.0008* | 0.0001* | 0.04 | 0.0001* |
| | 800 µg/ml | Mean ± | 85.00 ± | 87.67 ± | 90.34 ± | 93.33 ± | 96.67 ± | 99.67 ± |
| | | Sd | 2.65 | 2.08 | 2.08 | 2.89 | 0.58 | 0.58 |
| | | P. value | 0.008* | 0.0003* | 0.0001* | 0.21 | 0.42 | 0.0001* |
| ZIF-8/KIT-6 | 100 µg/ml | Mean ± | 36.33 ± | 40.33 ± | 44.67 ± | 49.33 ± | 56.67 ± | 63.33 ± |
| | | Sd | 0.58 | 1.15 | 1.15 | 0.58 | 0.58 | 1.15 |
| | | P. value | 0.0003* | 0.0006* | 0.0008* | 0.001* | 0.005* | 0.035 |
| | 200 µg/ml | Mean ± | 41.67 ± | 45.67 ± | 51.33 ± | 56.33 ± | 62.67 ± | 75.67 ± |
| | | Sd | 1.53 | 1.53 | 0.58 | 0.58 | 0.58 | 1.53 |
| | | P. value | 0.003* | 0.002* | 0.003* | 0.0045 | 0.034 | 0.135 |
| | 500 µg/ml | Mean ± | 49.33 ± | 54.67 ± | 58.67 ± | 64.67 ± | 78.33 ± | 85.33 ± |
| | | Sd | 0.58 | 1.15 | 1.53 | 1.53 | 2.08 | 0.58 |
| | | P. value | 0.005* | 0.021* | 0.053* | 0.047* | 0.033* | 0.211 |
| | 800 µg/ml | Mean ± | 72.67 ± | 76.33 ± | 77.67 ± | 81.67 ± | 86.67 ± | 91.33 ± |
| | | Sd | 1.15 | 3.06 | 2.52 | 2.52 | 2.08 | 0.58 |
| | | P. value | 0.008* | 0.100 | 0.021 | 0.072 | 0.15 | 0.40 |

Data were presented as the mean ± standard deviation (SD),
*P < 0.05 is statistically significant, compared to the parasite control.

To date, there is no full cure for Blastocystosis, an emerging parasitic disease. Small doses of metronidazole (as of 10 ug/ml) have been used as in-vitro anti-*Blastocystis* therapy, however, higher doses up to 1 mg/ml are typically required [Haresh, K., et. al., Isolate resistance of *Blastocystis hominis* to metronidazole., Trop Med Int Hlth., 1999, 4, 274-277, incorporated herein by reference in its entirety]. Here, a higher dose of 500 ug/ml of metronidazole was used as a comparison.

Resveratrol showed promising anti-protozoal activity, but its anti-*Blastocystis* activity has not yet been evaluated. Here, the in vitro effects of resveratrol and ZIF-8/KIT-6 nanocomponents on the viability of *Blastocystis* cysts were assessed. There was dose-dependent, and time depended anti-*Blastocystis* cysts activity for the two assessed nanocomposites at a low concentration. The MLC of resveratrol nanocomponents was 100 ug/ml, which is a very small dose than the higher doses tested before. Juan et al, reported that the prolonged eating (for 28 days) of large doses of resveratrol (1.4 gm), 1000 times the amount ingested daily by a human of 70 kg, causes no harm to rat as compared to rat control group. There were no histological, biochemical, or hematological changes in treated rats, also there was no change in habits of drinking water or consumption of food of treated rats, nor change of body weight [Juan, M. E., et. al., J Nutr., 2002, 132, 257-260, incorporated herein by reference in its entirety].

Studies have attributed the anti-protozoal activities of resveratrol and curcumin to reduced oxygen consumption by protozoa, which may explain its mechanism of action as anti-*Blastocystis* [Leiro, J., et. al., Antimicrob Agents Chemother., 2004, 48, 2497-2501; Kedzierski, L., et. al., Parasitol Res., 2007, 102, 91-97; Lamas, J., et. al., Vet Parasitol., 2009, 161, 307-315; & Vang, O., et. al., PLoS One, 2011, 6, e19881, each of which is incorporated herein by reference in its entirety]. There are many advantages to the nano-scaling of resveratrol and curcumin. It enhances their therapeutic activities by inducing cellular stress responses at lower doses. This low dose adaptive response is due to its nano-size with large surface area to volume ratio.

Giving the drug in lower doses reduces toxicity. In addition, with prolonged exposure, all nanocomposites killed *Blastocystis* cysts, this may be because nanocomposites accumulate in host cells and their action is sustained for a longer time.

The invention claimed is:

1. A method comprising:

orally administering a pharmaceutical composition comprising a nanomedicinal composition to a subject having a *Blastocystis* infection or *Blastocystis,* wherein the pharmaceutical composition is in the form of a tablet and comprises one or more selected from the group consisting of lactose, sucrose, a starch powder, a cellulose ester of an alkanoic acid, a cellulose alkyl ester, a talc, stearic acid, magnesium stearate, magnesium oxide, gelatine, acacia gum, and sodium alginate;

wherein the nanomedicinal composition comprises a nanocarrier comprising:

a metal organic framework which is a zeolitic imidazolate framework, and a porous silicate and/or aluminosilicate matrix;

an antioxidant disposed in the pores and/or on a surface of the nanocarrier; and wherein the antioxidant is Resveratrol in phenolic form, or Curcumin in enolic form.

2. The method of claim 1, wherein the porous silicate and/or aluminosilicate matrix is at least one selected from the group consisting of MCM-41 and KIT-6.

3. The method of claim 2, wherein the nanocarrier has a surface area of 225 to 750 $m^2/g$, a pore volume of 0.25 to 0.85 $cm^3/g$, and a mean pore size of 2 to 10 nm.

4. The method of claim 2, wherein the porous silicate and/or aluminosilicate matrix is MCM-41 and the nanocarrier has a surface area of 450 to 750 $m^2/g$, a pore volume of 0.25 to 0.65 $cm^3/g$, and a mean pore size of 2 to 4 nm.

5. The method of claim 2, wherein the porous silicate and/or aluminosilicate matrix is KIT-6 and the nanocarrier has a surface area of 225 to 450 $m^2/g$, a pore volume of 0.45 to 0.85 $cm^3/g$, and a mean pore size of 5 to 10 nm.

6. The method of claim 1, wherein the porous silicate and/or aluminosilicate matrix is present in an amount of 1 to 20 wt % based on a total weight of the nanocarrier.

7. The method of claim 1, wherein the metal organic framework comprises an imidazole of formula I:

(I)

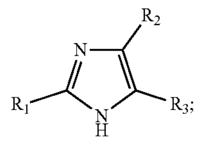

and is substantially free of a benzimidazole of formula II:

(II)

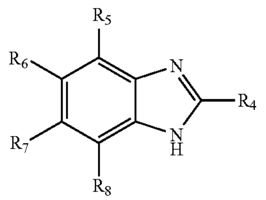

wherein $R_1$, $R_2$, $R_3$, $R_4$, $R_5$, $R_6$, $R_7$ and $R_8$ are each independently selected from the group consisting of a hydrogen, an optionally substituted alkyl, an optionally substituted cycloalkyl, an optionally substituted alkoxy, a hydroxyl, a halogen, a nitro, and a cyano.

8. The method of claim 7, wherein the zeolitic imidazolate framework is ZIF-8.

9. The method of claim 1, wherein the antioxidant is curcumin in enolic form.

10. The method of claim 1, wherein the antioxidant is resveratrol in phenolic form.

11. The method of claim 1, wherein the antioxidant is present in the nanomedicinal composition in an amount of 5 to 50 wt %, based on a total weight of nanomedicinal composition.

12. The method of claim 9, wherein the nanomedicinal composition releases greater than 20% of a total weight of curcumin within 24 to 72 hours of contact with a suitable biological medium.

13. The method of claim 10, wherein the nanomedicinal composition releases greater than 7.5% of a total weight of resveratrol within 24 to 72 hours of contact with a suitable biological medium.

* * * * *